(12) United States Patent
Argañarás et al.

(10) Patent No.: US 10,973,787 B2
(45) Date of Patent: Apr. 13, 2021

(54) BACTERICIDAL AND VIRUCIDAL PHARMACEUTICAL COMPOSITION

(71) Applicant: QUIMICA LUAR SRL, Cordoba (AR)

(72) Inventors: Luis Alberto Argañarás, Cordoba (AR); Adrian Javier Muñoz, Cordoba (AR); Roxana Valeria Alasino, Cordoba (AR); Ariel Gustavo Garro, Cordoba (AR); Dante Miguel Beltramo, Cordoba (AR)

(73) Assignee: Quimica Luar SRL, Córdoba (AR)

( * ) Notice: Subject to any disclaimer, the term of this patent is extended or adjusted under 35 U.S.C. 154(b) by 0 days.

(21) Appl. No.: 15/766,029

(22) PCT Filed: Oct. 4, 2016

(86) PCT No.: PCT/ES2016/070702
§ 371 (c)(1),
(2) Date: Apr. 5, 2018

(87) PCT Pub. No.: WO2017/060550
PCT Pub. Date: Apr. 13, 2017

(65) Prior Publication Data
US 2018/0296509 A1 Oct. 18, 2018

(30) Foreign Application Priority Data
Oct. 5, 2015 (AR) .............................. 20150103203

(51) Int. Cl.
*A61K 31/192* (2006.01)
*A61K 9/08* (2006.01)
*A61K 9/19* (2006.01)
*A61P 31/04* (2006.01)
*A61K 33/14* (2006.01)
*A61P 31/12* (2006.01)
*A61K 45/06* (2006.01)
*A61P 11/00* (2006.01)
*A61P 31/22* (2006.01)

(52) U.S. Cl.
CPC .............. *A61K 31/192* (2013.01); *A61K 9/08* (2013.01); *A61K 9/19* (2013.01); *A61K 33/14* (2013.01); *A61K 45/06* (2013.01); *A61P 11/00* (2018.01); *A61P 31/04* (2018.01); *A61P 31/12* (2018.01); *A61P 31/22* (2018.01)

(58) Field of Classification Search
None
See application file for complete search history.

(56) References Cited

U.S. PATENT DOCUMENTS

| 4,607,038 A | 8/1986 | Ogata et al. | |
|---|---|---|---|
| 5,856,345 A * | 1/1999 | Doi | A61K 9/0048 |
| | | | 514/350 |
| 5,885,597 A | 3/1999 | Botknecht et al. | |
| 7,186,186 B2 * | 3/2007 | Imahata | A63B 47/002 |
| | | | 221/268 |
| 7,186,417 B1 | 3/2007 | Siegel et al. | |
| 7,452,523 B2 * | 11/2008 | Hofmann | A61K 9/0075 |
| | | | 424/43 |
| 2008/0260863 A1 * | 10/2008 | Warner | A61K 33/14 |
| | | | 424/677 |
| 2012/0115897 A1 | 5/2012 | Tang et al. | |
| 2013/0178448 A1 | 7/2013 | Caparros-Wanderley et al. | |
| 2015/0105468 A1 * | 4/2015 | Martinez-Alzamora | ..................... |
| | | | A61P 29/00 |
| | | | 514/570 |

FOREIGN PATENT DOCUMENTS

| CN | 102138893 | 8/2011 |
|---|---|---|
| WO | 2012099479 | 7/2012 |

OTHER PUBLICATIONS

A.A.H.S. Al-Janabi. In Vitro Antibacterial Activity of Ibuprofen and Acetaminophen. Journal of Global Infectious Diseases, May-Aug. 2010, vol. 2, Issue-2, 105-108. (Year: 2010).*
International Search Report and written opinion dated Dec. 20, 2016 for PCT/ES2016/070702.
Al-Janabi Ali Abdul Husseins S "In vitro antibacterial activity of Ibruprofen and acetaminophen . . . Journal of global infectious disease" India May 2010 vol. 2.
Guzman, Juan D.,et al. "Antitubrecular specific activity of ibruprofen and the other 2-arylpropanoic acids using the HT-SPOTi whole-cell phenotypic assay". BMJ Open 2013, vol. 3, No. 6.
Lanas, A., Pique, J.M., Ponce, J., Gastroenterol. Hepatol., 24, 22 (2001); Gastroenterol. Hepatol., 24, 134 (2001).2.
Amphiphilic association of ibuprofen and two nonionic cellulose derivatives in aqueous solution—Annika Ridell, Hans Evertsson, Stefan Nilsson and Lars-Olof Sundeof—Journal of Pharmaceutical Sciences. vol. 88, Issue 11, pp. 1175-1181—Nov. 1999.
Celik I, Akbulut A, Kilic SS, Rahman A, Vural P, Canbaz M, Felek S. Effects of ibuprofen on the physiology and outcome of rabbit endotoxic shock. BMC infectious diseases. 2002;2:26-38.
Bernard GR, Wheeler AP, Russell JA, Schein R, Summer WR, Steinberg KP, et al. The effects of ibuprofen on the physiology and survival of patients with sepsis. New Engl J Med. 1997.
Sordelli DO, Cerquetti MC, el-Tawil G, Ramwell PW, Hooke AM, Bellanti JA. Ibuprofen modifies the inflammatory response of the murine lung to P. aeruginosa. Eur J Respir Dis. 198567118-27.

(Continued)

*Primary Examiner* — Michael P Cohen
(74) *Attorney, Agent, or Firm* — McCarter & English, LLP; Steven G. Davis; Zhongyu "Alex" Wang

(57) ABSTRACT

A bactericidal and virucidal pharmaceutical composition for use on epithelial tissues such as pulmonary, nasal and oral tissues, which comprises a non-steroidal anti-inflammatory drug (NSAID) in a concentration between 5 and 500 mM and a salt, being the NSAID preferably solubilized in a hypertonic saline solution applicable in therapies for viral infections of the Herpes simplex type. The composition can be used in therapies for herpes simplex viral infections, be used as a bactericidal mouthwash, or be vehiculated to the lung by using a nebuliser, for cystic fibrosis.

16 Claims, 19 Drawing Sheets

(56) References Cited

OTHER PUBLICATIONS

Graham DY, Klein PD, Opekun AR, Smith KE, Polasani RR, Evans DJ, et al. In vivo susceptibility of Campylobacter pylori. Am J Gastroenterol. 1989;84:233-8.

Byrne ST, Denkin SM, Zhang Y. Aspirin and ibuprofen enhance pyrazinamide treatment of murine tuberculosis. J Antimicrob Chemoth. 2007; 59:313-6.

Sordielli et al. (Sordelli DO, Cerquetti MC, el-Tawil G, Ramwell PW, Hooke AM, Bellanti JA. ibuprofen modifies the inflammatory response of the murine lung to Pseudomonas aeruginosa, Eur J Respir Dis. Aug. 1985;67(2):118-27.).

Dr. Ahmed Mohsen (Antibacterial Activity of Anti-biofilm Some Non-steroidal Anti-Inflammatory Drugs and N-acetyl Cysteine against Biofilm Producing Some Uropathogens—American Journal of Epidemiology and Infectious Disease, 2015, vol. 3, No. 1, 1-9).

Dr. Cidalia Pina-Vaz et al.(Antifungal activity of ibuprofen alone and in combination with fluconazole against *Candida* species Journal Medical Microbiology—vol. 49 (2000) 831-840).

Journal of Aerosol Medicine and Pulmonary Drug Delivery in Mar. 2009: "Analgesic Effect from Ibuprofen Nanoparticles Inhaled by Male Mice."

Alasino Characterization of the Inhibition of Enveloped Virus Infectivity by the Cationic Acrylate Polymer Eudragit E100 et al., Macromol. Biosci. 2007, 7, 1132-1138.

Reed-Muench method of analysis (Reed LJ, H. Munch, Am. J. Hygiene 1938 27, 493.).

* cited by examiner

BACTERICIDAL AND VIRUCIDAL PHARMACEUTICAL COMPOSITION

RELATED APPLICATIONS

This application is the US national phase application of international application number PCT/ES2016/070702, filed 4 Oct. 2016, which designates the US and claims priority to Argentinian application AR 20150103203 filed 5 Oct. 2015, the contents of each of which are hereby incorporated by reference as if set forth in their entireties.

FIELD OF THE INVENTION

The present invention relates to pharmaceutical compositions for the treatment of pulmonary diseases and of epithelial tissue, such as cystic fibrosis. In particular, this invention is a composition meant for topic use or nebulisations.

STATE OF THE ART

Non-steroidal anti-inflammatory drugs (NSAIDs) are a heterogeneous group of drugs which share their therapeutical action (analgesic, anti-inflammatory and antipyretic effect) but differ in their relative toxicity and efficacy.

Although NSAIDs are relatively safe are drugs, when administered in suitable doses and to selected patients they may present potentially severe adverse effects and interactions. The side effects caused by NSAIDs affect various organs, but those generated at the gastrointestinal level are the most frequent ones. About 2-3% of patients taking NSAIDs for a year develop gastrointestinal complications such as bleeding, or upper or lower perforation. Over that period, 5-10% desarrollan úlceras sintomáticas y un 30-50% desarrollan dispepsia que requiere atención médica [Lanas, A., Pique, J. M., Ponce, J., *Gastroenterol. Hepatol.*, 24, 22 (2001); *Gastroenterol. Hepatol.*, 24, 134 (2001). 2].

An ibuprofen molecule with a MW 206.3 g/mol, (FIG. 1) as well as other derivatives of 2-arylpropionate, which include ketoprofen, flurbiprofen, naproxen, etc., contains a chiral carbon in the α (alpha) position of the propionate.

Ibuprofen is considered a non-steroidal anti-inflammatory agent (NSAID) frequently used as antipyretic and for the symptomatic relief of headache (cluster), dental pain, muscle pain or myalgia, menstrual discomfort, mild neurological pain, and post-surgical pain. It is also used to treat inflammatory conditions such as those present in arthritis, rheumatoid arthritis and gouty arthritis. Generally, the recommended adult dose is about 1200 mg daily. However, under medical supervision, the maximum amount of ibuprofen for adults is 800 mg per dose or 3200 mg per day.

There is little correlation between the severity of symptoms and the plasma levels measured. Toxic effects are unlikely to appear with doses below 100 mg/kg but they can be severe above 400 mg/kg (about 150 tablets of 200 mg for a normal patient). However, high doses do not indicate that the clinical features are to be lethal. It is not possible to determine a precise lethal dose, since it can vary with age, weight and associated disease in patients.

Most symptoms are an excess of action and include abdominal pain, nausea, vomiting, dizziness, drowsiness, headache, tinnitus and nystagmus. Symptoms may be rarely more severe, being some of them gastrointestinal bleeding, seizures, metabolic acidosis, hyperkalemia, hypotension, bradycardia, tachycardia, atrial fibrillation, coma, liver failure, acute renal failure, cyanosis, respiratory depression and cardiac arrest.

Ibuprofen, in structure, is a substantially water-insoluble molecule. It solubilizes less than 1 mg in 1 mL of water (<1 mg/mL). The form of administration of ibuprofen for the treatment of all the cases mentioned above is always in tablets or soft capsules in which ibuprofen is found in protonated form. Therefore, such protonated form renders ibuprofen a markedly water-insoluble molecule. As a counterpart, ibuprofen is soluble in organic solvents such as ethanol or acetone.

Ibuprofen may be solubilised in water by removing the proton by some cation. In this regard, an aqueous solution up to concentrations of 1 M pH 7.0-8.5, titrating ibuprofen with alkaline solutions of sodium hydroxide, potassium hydroxide, magnesium hydroxide may be prepared, or else diethanolamine, tris (hydroxymethyl) aminomethane (THAM) or arginine, lysine or histidine may be added.

Because of its molecular structure, once solubilised in water and depending on its concentration, ibuprofen becomes an amphipathic molecule with surfactant properties with two forms or structures, one below its critical micelle concentration (CMC) that is about 180 mM (Amphiphilic association of ibuprofen and two nonionic cellulose derivatives in aqueous solution—Annika Ridell, Hans Evertsson, Stefan Nilsson and Lars-Olof Sundeof—Journal of Pharmaceutical Sciences. Volume 88, Issue 11, pages 1175-1181—November 1999) and another over its CMC, where it is found forming a micelle.

In vitro studies indicate that, like other NSAIDs, ibuprofen is largely bound to plasma albumin, although in babies, this appears to be significantly lower (95%) compared with adult plasma (99%). Ibuprofen competes with bilirubin binding to albumin. Especially in the serum of newborn babies, this could result in the increased free fraction of bilirubin at high concentrations of ibuprofen.

Hussein and Janabi have recently published an article (In Vitro Antibacterial Activity of ibuprofen and Acetaminophen, J Glob Infect Dis. 2010 May-August; 2(2): 105-108), in which in vitro antibacterial activity of ibuprofen and acetaminophen is discussed. The article mentions that ibuprofen limits its bactericidal activity only to bacteria such as *Escherichia coli* (Celik I, Akbulut A, Kilic S S, Rahman A, Vural P, Canbaz M, Felek S. Effects of ibuprofen on the physiology and outcome of rabbit endotoxic shock. BMC infectious diseases. 2002; 2:26-38. Bernard G R, Wheeler A P, Russell J A, Schein R, Summer W R, Steinberg K P, et al. The effects of ibuprofen on the physiology and survival of patients with sepsis. New Engl J Med. 1997. In this case it is proved that ibuprofen presents its anti-inflammatory activity on the lungs of rabbits infected with *Pseudomonas aeruginosa*, but does not have effects on the bacteria itself (Sordelli D O, Cerquetti M C, el-Tawil G, Ramwell P W, Hooke A M, Bellanti J A. Ibuprofen modifies the inflammatory response of the murine lung to *P. aeruginosa*. Eur J Respir Dis. 198567118-27. Such work also shows that ibuprofen does not present activity on *ampylobacter pylori* in humans (Graham D Y, Klein P D, Opekun A R, Smith K E, Polasani R R, Evans D J, et al. In vivo susceptibility of *Campylobacter pylori*. Am J Gastroenterol. 1989; 84:233-8] y sobre *Mycobacterium tuberculosis* in rats (Byrne S T, Denkin S M, Zhang Y. Aspirin and ibuprofen enhance pyrazinamide treatment of murine tuberculosis. J Antimicrob Chemoth. 2007; 59:313-6). In this study a significant activity of ibuprofen is not shown since no effect was observed on bacteria type *Serratia* or *Bacillus subtilis*, and the authors present a varying inhibitory activity of ibuprofen. It is worth mentioning that the in vitro studies were conducted vehiculizing ibuprofen in ethanol, a condition that causes precipitation of ibuprofen itself when the stock solution is diluted in aqueous medium.

The research work developed by Sordielli et al. (Sordelli D O, Cerquetti M C, el-Tawil G, Ramwell P W, Hooke A M, Bellanti J A. ibuprofen modifies the inflammatory response of the murine lung to *Pseudomonas aeruginosa, Eur J Respir Dis*. 1985 August; 67(2):118-27.) shows that the injection of ibuprofen sodium is able to reduce the inflammatory ability caused by pulmonary infection by *P aeruginosa*, but it does not affect the biological activity of bacteria.

A recent work Juan D Guzman et al. (BMJ open Jun. 5, 2015 "antitubercular specific activity of ibuprofen and the other 2-arylpropanoic acids using the HT-spoti whole-cell phenotypic essay) shows that a formulation of ibuprofen and other anti-inflammatory non-steroidal drugs present bactericidal properties for treatment of tuberculosis. Using a test called HT-SPOTi they demonstrate that ibuprofen is antibiotic, but an even more active derivative 3,5-dinitro-Ibuprofen appears.

Another paper published by the group of Dr. Ahmed Mohsen (Antibacterial Activity of Anti-biofilm Some Non-steroidal Anti-Inflammatory Drugs and N-acetyl Cysteine against Biofilm Producing Some Uropathogens—American Journal of Epidemiology and Infectious Disease, 2015, Vol. 3, No. 1, 1-9) shows that drugs like NSAIDs and N-acetyl cystein adversely affect the adherence of bacteria *Staphylococcus aureus, Klebsiella pneumoniae, Proteus mirabilis* and *P. aeruginosa* to the surface of catheters for urological use, which avoids undesired biofilms, and also present a significant bactericidal effect, which can be very beneficial for the treatment of infections caused by the use of catheters.

Research done by Dr. Cidalia Pina-Vaz et al. (Antifungal activity of ibuprofen alone and in combination with fluconazole against *Candida* species Journal Medical Microbiology—Vol 49 (2000) 831-840), it is shown that ibuprofen, alone or in combination with fluconazole, may cause a significant antifungal effect on different strains of *Candida*, affecting the stability of the membrane so as to produce a marked release of intracellular K affecting the viability of the fungus.

Another patent, US20120115897 A1, describes the formation of a complex between ibuprofen and derivatives of esters of ascorbic acid and shows that this formulation can enhance water solubility, facilitating intravenous administration reducing application time, thereby lowering its undesired effect at the gastrointestinal level, increasing its penetration into the blood-brain barrier and it can be applied in various diseases such as arthritis, multiple sclerosis, cystic fibrosis, and pneumonia in the treatment of patent ductus arteriosus in premature infants, problems of cerebral hypoxia and certain cancers.

A common practice in the art is preparing ibuprofen in methanol, which allows precipitation in the dilution of the solutions. Also, this NSAID is commonly used in injectable form, which results in two problems. The first is that sodium ibuprofen has a strong hemolytic effect, and second is that ibuprofen rapidly interacts with albumin, the major plasma protein that when forming a complex strongly inhibits its bactericidal activity as it is demonstrated in the studies herein, where it is clearly shown that, depending on the concentration of albumin present in the medium, the bactericidal activity of ibuprofen decreases.

In addition, US 20130178448 A1 discloses a formulation of oral administration of ibuprofen which is in the presence of different types of lipids such as triglycerides or other fatty acids and alcohol, which can be administered as a liquid or tablets to be ingested orally by animals so that they may reach high levels of ibuprofen in blood in the treatment of lung diseases. It is herein demonstrated that when ibuprofen is solubilised in a triglyceride emulsion, as it happens in its interaction with albumin, it completely loses its bactericidal activity.

As previously mentioned, when ibuprofen is solubilised in water it acquires surfactant properties. Therefore, it can interact with lipid membranes affecting its stability. The interaction between ibuprofen and lipids and also its toxicity depends on the aggregation state of ibuprofen. It has been mentioned that at concentrations above its CMC, ibuprofen can damage the integrity of lipid membranes.

On the other hand, there is a history of the use of saline solution for the treatment of airway disorders by nebulisation. Particularly, for the treatment of cystic fibrosis nebulisation with antibiotics is used, being tobramycin the most common one. Furthermore, there is a history of the use of ibuprofen as an anti-inflammatory drug for the same conditions, but usually by oral or intravenous administration. It is worth highlighting that patients with cystic fibrosis, in general children, the continuous use of NSAIDs causes adverse effects that often worsen the pathological condition. In addition, as detailed herein there is history suggesting the use of ibuprofen as a bactericidal drug, although the prior art suggests that it would not be suitable for use against *P. aeruginosa* and against *Burkhordelia cepacia*. Finally, an article in Journal of Aerosol Medicine and Pulmonary Drug Delivery in March 2009: "Analgesic Effect from Ibuprofen Nanoparticles Inhaled by Male Mice" discloses the nebulisation of solid ibuprofen carried in steam to rats, to assess its anti-inflammatory effect and demonstrate that it requires 3 to 5 times less concentration to have an effect equivalent to that in oral doses.

The present invention provides a composition that can be administered by nebulisation to treat cystic fibrosis, which presents an unexpected and surprising effect by acting as a bactericide for type Gram+ and Gram− bacteria, especially by inhibiting bacteria such as *P. aeruginosa, S. aureus, B cepacia* and also having virucidal effect on those lipid-enveloped viruses. The composition of the present invention is very simple and its side effects are negligible, compared with the continuous use of common antibiotics for the treatment of this disease. One of the technical effects of the present invention is that the bactericidal effect of ibuprofen increased 5 times for being in hypertonic NaCl solution, as it can be seen in Example 11 herein. Moreover, providing the examples herein, the inventors have shown the ability of ibuprofen above and especially below its critical micelle concentration (CMC), to destabilize membranes of different Gram+ and Gram− bacteria and lipid-enveloped viruses, affecting their biological activity, allowing redefining, thanks to the present invention, ibuprofen as a bactericidal and virucidal agent, in combination with a saline solution.

BRIEF DESCRIPTION OF THE INVENTION

The bactericidal and virucidal pharmaceutical composition, to be applied to epithelial tissue, such as lung, nose and mouth, the main object of the present invention, comprises an anti-inflammatory drug (NSAID) in a concentration between 5 and 500 mM solubilised in saline solution, preferably hypertonic comprising a concentration of between 0.3 and 2 Molar NaCl can be CIK; more preferably between 0.4 and 1, 1 Molar NaCl; even more preferably between 0.9 and 1, 05 Molar NaCl. Its administration form is selected from the group comprised by inhalation, nebulisation, mouthwash and topical administration. Wherein said anti-inflammatory drug (NSAID), preferably comprises a concentration between 5 and 180 mM; more preferably less than 180 mM; even more preferably between 5 and 50 mM. Wherein said non-steroidal anti-inflammatory is arylpropionic selected from the group comprised by ibuprofen, naproxen, flurbiprofen, ketoprofen, diclofenac, diflunisal, etodolac, fenoprofen, indomethacin, meclofenamate, mefenamic acid, meloxicam, nabumetone, oxaprozin, piroxicam, sulindac, tolmetin, celecoxib, acetylated salicylates, non-acetylated salicylates, and combinations thereof; preferably ibuprofen. And where their counterions are monovalent cations selected from the group comprised of sodium, potassium, lithium and combinations thereof. Furthermore, it said composition comprises a pH in aqueous solution between 6.0 and 8.5; preferably between 7.0 and 8.0; more preferably between 7.5 and 7.9.

Furthermore, the present invention may be embodied either in liquid or as a powder or lyophilised by drying or lyophilisation respectively from the hypertonic aqueous solution of said pharmaceutical composition.

In a preferred embodiment the present invention further comprises an anesthetic agent selected from the group comprised by xylocaine, lidocaine, carticaine, mepivacaine and mixtures thereof.

The present invention is a pharmaceutical composition for the treatment of cystic fibrosis in nebulised application to reach the lungs, as well as for the treatment of viral infections Herpes simplex type, applied to affected skin. It can also be used as a bactericidal mouthwash.

In a preferred form of implementing the present invention for the treatment of cystic fibrosis said pharmaceutical composition is in the absence of usual antibiotics for this disease. These usual antibiotics include among others, colistimethate sodium, tobramycin, ciprofloxacin, lysine, levofloxacin, ciprofloxacin aztreonam, fosfomycin, amphotericin B, vancomycin, gentamicin, ceftazidime, ampicillin and amikacin and mixtures thereof.

In another alternative to implement the present invention, said composition further comprises said usual antibiotics.

The process of manufacturing said bactericidal and virucidal pharmaceutical composition to be applied on epithelial tissues, such as pulmonary, nasal and oral tissue, another object of the present invention comprises the following steps:

A. said NSAID is mixed with water and stirred to maintain the suspension of the NSAID;

B. NaOH is added until a pH between 6.8 and 8.5 is reached by gentle stirring, so as to allow complete solubilisation of said NSAID to a concentration of between 1 and 100 mg/mL; preferably allowed to stand at room temperature for at least 12 h;

C. a hypertonic NaCl saline solution is added to the preparation in step B., at a concentration of 0.3 to 2 M;

D. the preparation in step D. is filtered through 0.22-micron pore filter.

In a preferred embodiment of the present invention, said process further comprises the following step:

E. the filtered solution of step D. is lyophilised;

Finally, after step E it is possible to add the next step:

F. when applied either to be vehiculated to the lungs by nebuliser or to be applied to the mouth as a mouthwash, the lyophilised composition of step E. is resuspended in water or in a 5% glucose solution.

The present invention provides a bactericidal and virucidal pharmaceutical composition to be applied on epithelial tissues, such as pulmonary, nasal and oral tissue, comprising a non-steroidal anti-inflammatory drug (NSAID) and a salt. Where it preferably comprises a molar ratio of said NSAID and said salt of between 1:0.6 and 1:400, more preferably between 1:10 and 1:100 and wherein said salt is selected from the group comprising sodium chloride, potassium and combinations thereof. And preferably such composition comprises a pharmaceutical formulation to be diluted in water in the absence of any other component. And where preferably it comprises a pharmaceutical formulation for the treatment of cystic fibrosis. And where preferably it comprises a pharmaceutical formulation for the treatment of Herpes Simplex. And where preferably comprises a pharmaceutical formulation for mouthwash.

DETAILED DESCRIPTION OF THE INVENTION

Figure 1:
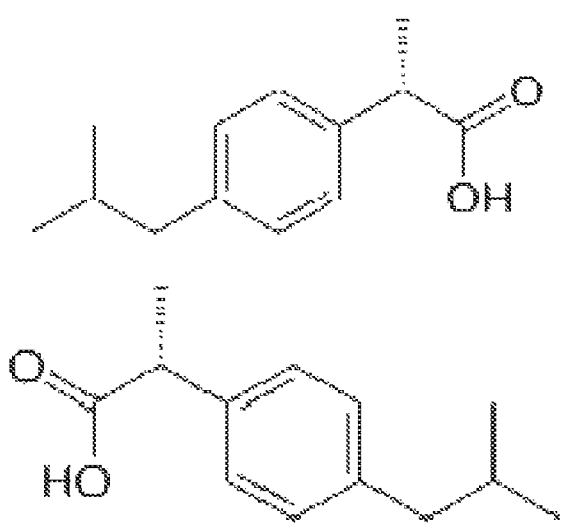
FIG. 1: Chemical structure of ibuprofen

The bactericidal pharmaceutical composition, which also has virucidal effects, which is to be applied on epithelial tissues, such as pulmonary, nasal and oral tissue, the main object of the present invention comprises a non-steroidal anti-inflammatory drug (NSAID) and a salt; wherein said NSAID is in a concentration between 5 and 500 mM and solubilised in saline solution of said salt. Wherein said saline solution is preferably hypertonic comprising a concentration of between 0.3 and 2 Molar of a salt that is preferably NaCl, but can be any salt suitable for human consumption such as potassium chloride; more preferably between 0.4 and 1, 1 Molar NaCl; even more preferably between 0.9 and 1, 05 Molar NaCl. Its administration form is selected from the group comprised by inhalation, nebulization, mouthwash and topical administration. Wherein said non-steroidal anti-inflammatory drug (NSAID), preferably comprises a concentration between 5 and 180 mM; more preferably less than 180 mM; even more preferably between 5 and 50 mM. Wherein said non-steroidal anti-inflammatory agent is selected from the group comprised by ibuprofen, naproxen, flurbiprofen, ketoprofen, diclofenac, diflunisal, etodolac, fenoprofen, indomethacin, meclofenamate, mefenamic acid, meloxicam, nabumetone, oxaprozin, piroxicam, sulindac, tolmetin, celecoxib, acetylated salicylates, non-acetylated salicylates, and combinations thereof; preferably ibuprofen. And where their counterions are monovalent cations selected from the group comprised of sodium, potassium, lithium and combinations thereof. Furthermore, said composition comprises a pH in aqueous solution between 6.0 and 8.5; preferably between 7.0 and 8.0; more preferably between 7.5 and 7.9.

In a preferred embodiment of the present invention said pharmaceutical composition comprises ibuprofen or sodium ibuprofen in a concentration of 50 mM in a hypertonic saline solution 1 M of NaCl.

Furthermore, the present invention may be prepared either in liquid state or as a powder or lyophilised by drying or lyophilisation, respectively from the hypertonic aqueous solution of said pharmaceutical composition. Both the drying process and the lyophilisation of pharmaceutical compositions is well known in the prior art, therefore providing further details on the subject is not considered necessary.

In a preferred embodiment, the present invention further comprises an anesthetic agent. The anesthetic effects of the composition of the present invention soothe the pain and discomfort caused by cystic fibrosis, but it is mainly beneficial when used for the treatment of viruses such as Herpes. Such anesthetic agent can be any of the accepted ones for pharmaceutical use.

Among those anesthetics preferred for the present invention, the following can be mentioned: xylocaine, lidocaine, carticaine, mepivacaine and the mixtures thereof.

The present invention is a pharmaceutical composition which is useful for the treatment of cystic fibrosis in nebulised application to reach the lungs. In this really serious disease affecting mainly children, the present invention has advantages that had never been reported before, since with very low doses of NSAIDs not only anti-inflammatory but also bactericidal and virucidal effects are achieved, without generating resistant mucus and acting even if it already exists. The present invention is also applicable in the treatment of Herpes simplex type viral infections, applied to affected skin. The present invention is also effective as bactericidal oral rinse. The combination of ionic strength with the presence of NSAIDs at very low doses achieves a bactericidal and virucidal effect that has never been reported before. Technically, using very low concentrations of NSAIDs results in a dramatic reduction of the common adverse effects of these anti-inflammatory drugs.

In a preferred embodiment of the present invention to treat cystic fibrosis said pharmaceutical composition is free from the usual antibiotics for this disease. Such usual antibiotics are, among others, colistimethate sodium, tobramycin, ciprofloxacin, lysine, levofloxacin, ciprofloxacin aztreonam, fosfomycin, amphotericin B, vancomycin, gentamicin, ceftazidime, ampicillin and amikacin and the mixtures thereof.

In another alternative embodiment of the present invention, said composition further comprises said usual antibiotics.

The process of manufacturing said bactericidal and virucidal pharmaceutical composition for application on lung, nose and mouth epithelial tissues, another object of the present invention comprises the following steps:

A. said NSAID is mixed with water and stirred to maintain suspension of the NSAID;

B. NaHO is added until a pH between 6.8 and 8.5 is reached by gentle stirring, so as to allow complete solubilisation of said NSAID to a concentration of between 1 and 100 mg/mL;

C. It is allowed to stand at room temperature for at least 12 hours;

D. a hypertonic NaCl saline solution is added to the preparation in step C., at a concentration of 0.2 to 2 M;

E. the preparation is filtered through 0.22-micron pore filter.

In a preferred embodiment of the present invention, said process further comprises the following step:

F. the filtered solution of step E. in claim 11 is lyophilised;

Finally, after step F it is possible to add the next step:

G. when applied either to be vehiculated to reach the lungs by means of a nebuliser or to be applied to the mouth as a mouthwash, the lyophilised composition of step f. is resuspended in distilled water or in a 5% glucose solution.

Tests to Characterize the Bactericidal Properties of NSAIDs and of the Composition of the Present Invention.

There are numerous and varied laboratory methods that can be used to determine in vitro the susceptibility of bacteria to various antimicrobial agents such as plaque assays of inhibitory growth halos, growth/inhibition test in nutrient broths, commercial kits, antibiograms, etc.

In this case, tests were run on a non-nutritive liquid carrier (buffer solution) wherein the antimicrobial agent is mixed with quantified inocula of pure bacterial cultures. After different incubation times, the material is seeded on agar plates to perform quantification assays on the number of bacterias surviving the treatment.

The examples detailed below describe an overview of the tests, and contains among others, the preliminary activities of conditioning of strains, work supplies, materials and methods and analysis of the results obtained from biological activity.

Tests to Characterize the Virucidal Properties of NSAIDs and of the Composition of the Present Invention.

For the assessment of virucidal activity of NSAIDs, preferably ibuprofen, tests were conducted as described in Alasino et al in 2007. In this case, the various strains of virus with lipid envelope are incubated with increasing amounts of ibuprofen for a period ranging between 60 and 120 minutes. This material was then incubated with cultured cells which are susceptible to attack by these viruses, showing a marked cytopathic effect (cell aggregates (rosettes) or cell death) that can be detected by observation under the optical microscope.

Potential Applications of the Present Invention to Various Infectious Diseases

The present invention provides a composition of ibuprofen sodium alone or associated with a hypertonic saline pH between 6.8 and 8.2, having bactericidal properties against different bacteria such as *Pseudomonas aeruginosa, Burkhordelia cepacia, Pseudomonas fluorescens, Enterobacter aerogenes, Klebsiella pneumoniae, Escherichia coli, Bacillus subtilis* (Gram+), *Staphylococcus aureus* (Gram+), *Enterococcus faecalis* (Gram+) and virucidal properties which produce the inactivation of those lipid-enveloped viruses such as, bovine diarrhea virus, Herpes types I and II, vesicular stomatitis virus, hepatitis C virus, varicella virus.

Applications of the composition of the present invention with bactericidal and virucidal properties may be used in the treatment of infectious diseases of the bacterial type that directly affect mucosa such as oral or pulmonary mucosa, or else viral diseases as infections by Herpes type I, on lips, mouth or vaginal level, as well as in the case of the cutaneous expression of Herpes virus type II.

Advantages of the Composition of the Present Invention in Treating Various Infections The bactericidal properties of an IBU solution alone, preferably in combination with a hypertonic solution, is beneficial to treat bacterial infections, especially those at the lung level caused by bacteria such as *P aeruginosa*, which is capable of producing biofilms, as in the case of cystic fibrosis, a disease that is very difficult to cure. The composition of the present invention can be in liquid form, which makes it likely to be applied by a standard nebulisation system. Nebulisers are the devices of choice for pulmonary administration of drugs. Current nebulisers work by ultrasonic pulses applied to a solution meant to form a cloud where the drugs to be vehiculated are found. Patients breath in this cloud normally for several minutes until the solution is exhausted, normally 1 to 5 mL by nebulisation, which has some advantages as follows:

- In this case the drug would reach the lungs directly, rendering concentration in the target organ more effective in order to act on the bacteria *P. aeruginosa, S aureus*, methillicin resistant and *B cepacia* as detailed in the examples mentioned below.
- This would avoid the systemic use of antibiotics and NSAIDs because when entering blood, the dilution affecting the effective concentration in the target organ occurs.
- It prevents the NSAID coming into contact with plasma components and more specifically with the protein albumin with which it interacts strongly and could reduce its bactericidal activity.
- Considering that IBU is a molecule of anionic nature, it does not present interaction with strongly anionic biopolymers such as alginate and DNA, major materials present in the biofilm that appears in this pathology, as it can occur with antibiotics currently used such as tobramycin (FIG. 2) having five primary amino groups in its structure.
- The fact that the present invention comprises ibuprofen together with a solution of high ionic strength, allows as it is shown herein, increasing effectiveness of bactericidal power 5 times, reducing the contact time to develop its bactericidal property from hours to a few minutes.
- The composition of the present invention, while presenting a hypertonic saline solution allows it to act not only as a biofilm fluidizing agent, but also presents a sound bactericidal effect, in addition to its anti-inflammatory effect already known.

In the particular case of the bactericidal effect of the composition of the present invention on the oral epithelium, the advantage of this formulation against current antiseptic formulations lies in that those which use chlorhexidine eventually cause teeth coloring, while this does not happen with the use of ibuprofen. Moreover, the composition of the invention can be used for buccal or labial infections caused by Herpes Simplex Type I viruses since in addition to its antiviral effect it provides anti-inflammatory effect during treatment, a desired condition to reliever discomfort during infection.

Manufacturing Process of the Composition of the Present Invention

Said composition of the invention comprises at least one bioactive agent such as NSAIDs solubilised in aqueous medium in addition to the classical anti-inflammatory property, in the present invention exhibits bactericidal and virucidal properties when said NSAID is formulated at a concentration below its critical micelle concentration and in the presence of saline solution. The manufacturing process of said composition comprises for instance, the following steps:

- NSAID is placed in a container into which water is added; it is then stirred to maintain NSAIDs in suspension,
- a basic solution such as NAHO is subsequently added to reach a pH between 7.0 and 8.5 stirring gently, so as to allow complete solubilisation of said NSAID. Preferably, it is allowed to rest at room temperature for at least 12 hours,
- the preparation is diluted to reach the desired concentration of NSAID for the treatment chosen,
- a NaCl saline solution is added to the previous preparation, comprised within a 0.2 to 2 M range,
- the preparation is passed through a 0.22-micron pore size filter,
- the sterilized material can be finally lyophilised for preservation or else kept in liquid state until it is used.
- Finally, at the time of application, either to be vehiculated to the lungs by means of a nebuliser, or to be applied to the mouth as a mouthwash, the lyophilised NSAID is resuspended in the original volume of: a—distilled water, b—in a 5% glucose solution.

Said NSAIDs may be selected from the group comprised by arylpropionic selected from the group comprised by ibuprofen, naproxen, flurbiprofen, ketoprofen, diclofenac, diflunisal, etodolac, fenoprofen, indomethacin, meclofenamate, mefenamic acid, meloxicam, nabumetone, oxaprozin, piroxicam, sulindac, tolmetin, celecoxib, acetylated salicylates, non-acetylated salicylates, and combinations thereof.

Salts of said NSAIDs such as Na, I or K are preferred. Therefore, when adding sodium hydroxide solution is added, NSAID salt is formed. Preferably, sodium ibuprofen (IBU-Na) is used, for it presents greater solubility in aqueous solution than protonated ibuprofen (IBU-H).

The composition of the present invention comprises powder NSAID, preferably sodium ibuprofen, and Na or K salt in a molar ratio of NSAID:salt of 1:0.6 and 1:400, preferably between 1:10 and 1:100.

This powder may be diluted in water to obtain the pharmaceutical formulation of the invention.

In this detailed description, IBUPROFEN means ibuprofen in any of its forms. In particular, PROTONATED IBUPROFEN is to be identified with the following name: IBU-H.

While SODIUM IBUPROFEN, also known as SODIUM IBUPROFENATE or IBUPROFEN SODIUM SALT shall be identified as IBU-Na herein. This sodium ibuprofen can be free of water in mono hydrate or dihydrate form.

EXAMPLES

Example 1

Preparation of Solutions for Tests Performed Herein and in the Following Examples.

Next, methods of preparation of the components used for the embodiment of the present invention, which prove to be the best known to the inventors are described, but they are not the only possible ones.

Preparation of IBU-H Solutions:

Solid ibuprofen is dissolved (20 g in pure ethanol up to 100 mL); this represents IBU-H 1M solution. Studies on the activity of these formulations use a solution that placed on the culture medium does not exceed 5% ethanol concentration which does not affect the viability of bacteria.

IBU-Na Solution Preparation:

IBU-Na stock solution is prepared by weighing 20 g of ibuprofen, adding water to 50 mL, and then adding enough NAHO 4M solution to reach a pH between 7 and 8; finally it is made up to 100 mL to a final concentration of 1 M Na-IBU.

Naproxen Solution Preparation:

Naproxen stock solution is prepared by weighing 23 g of Naproxen, adding water to 50 mL, and then adding enough NAHO 4M solution to achieve a pH between 7 and 8; finally it is made up to 100 mL to reach a final concentration of 1 M Naproxen.

Preparation of the Favorite Composition of the Present Invention:

The following examples show the steps followed to obtain the various solutions used:
  a. 2 g of ibuprofen are placed in an Erlenmeyer that is added with 5 mL of water and stirred to maintain the ibuprofen suspension,
  b. then NAHO 4 M is added to reach a pH comprised between 7.0 to 8.5 stirring gently, so as to allow complete solubilisation of IBU and it is finally made up to 10 mL to achieve a concentration of 200 mg/mL. It is allowed to stand at room temperature for at least 12 hours.
  c. The preparation is diluted to reach the desired IBU-NA concentration for the treatment chosen, as in the example.
  d. The hypertonic saline solution is added to the preparation mentioned above to reach a concentration of 1 M NaCl.
  e. The preparation is filtered through a 0.22-micron pore filter.

To obtain the composition of the present invention for use in the tests performed in the following examples, compositions ranging from 1 to 100 mM of IBU-Na and hypertonic solutions, which present a final concentration of 1 M NaCl, are obtained following the procedure described. The procedures followed are the usual laboratory practices to perform dilutions.

Example 2

Activation and Conservation of Bacterial Strains Stock

Lyophilised commercial strains ATCC (KWIK-STIK MicroBioLogics) activated in tubes containing 10 mL of Brain Heart Infusion BHI (Biokar BK015HA) at 37° C. for 24 hours were used.

Composition in g/L:

| | |
|---|---|
| Brain and heart Infusion | 17.5 |
| Peptone | 10 |
| Glucose | 2 |
| Sodium chloride | 5 |
| Disodium phosphate | 2.5 |

Preparation: 37 g of medium formulated in 1 L of distilled water were dissolved, heated until completely dissolved and adjusted in pH to 7.4±0.2 at 25° C.; finally, it is autoclaved for sterilization for 15 minutes at 121° C.

After the activation time of each strain in said means and having observed effective growth by turbidity close to 0.5 scale Mc Farland's standard, 10% v/v sterile glycerol as cryoprotectant was added to each culture. Subsequently, the content of each tube was distributed in 1 ml aliquots in 1.5 mL eppendorf tubes. These strains were identified as stock strains and stored at ultra low temperature in a freezer at −70 (Sanyo MDFU70V Ultra low temperature freezer) to provide an adequate reserve of each stock strain.

Example 3

Antimicrobial Activity Tests of IBU

Figure 2:
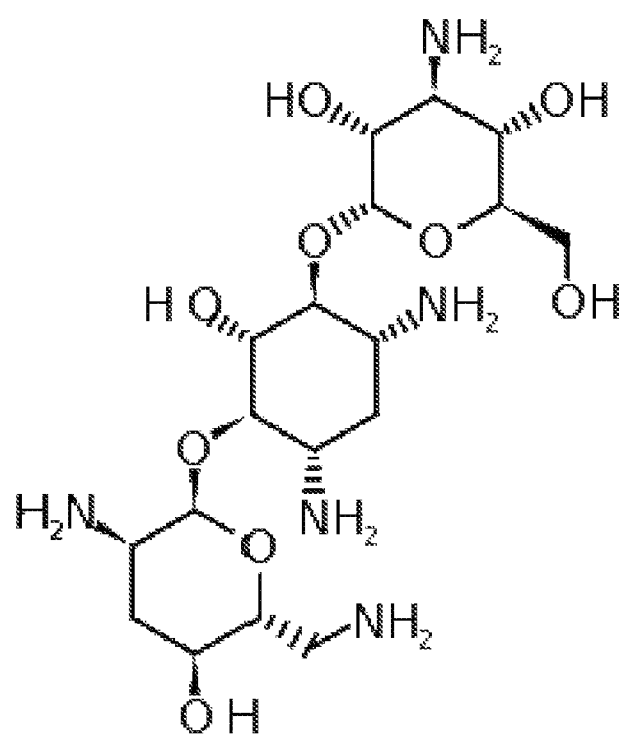
FIG. 2: Chemical structure of tobramycin

IBU effectiveness testing at different concentrations, times of action, ionic strength, pH variations and various bacterial populations were performed; effective concentrations of commercial tobramycin antibiotic (FIG. 2) were also measured.

Test Methodology

Work consisted of incubating bacterial populations of a known load in terms of CFU/mL with the compounds mentioned in different molar concentrations. In vitro test batteries were organized at different doses or concentrations and in 1.5 mL Eppendorf tubes without the addition of culture medium. To this purpose, a PBS 100 mM phosphate buffer was used to maintain physiological conditions throughout the period of each test at 37° C.

PBS 100 mM Buffer Composition:

| |
|---|
| 8 g (137 mM) NaCl |
| 0.2 g (2.7 mM) KCl |
| 1.44 g (10 mM) NaHPO |
| 0.24 g (2 mM) KH2PO |
| 1000 mL Milli Q water |

When the time for each assay finished, aliquots of 100 uL and decimal dilutions of each tube which were seeded on petri dishes for the direct count of colony forming units (CFU) in Mueller Hinton agar (MHA), using pour-plating or spread-plating standard methods.

Each plate was added with 5 uL of a solution of 2,3,5-metabolic dye triphenyltetrazolium of chloride (TTC) 1% to enhance the contrast of colonies. Plates were incubated in inverted position, in a culture stove for 24-48 hours at 37° C. and subsequently the direct count was done, adjusted by dilution factors and seeding to report results in terms of CFU/mL.

The medium composition in g/L is:

| | |
|---|---|
| Peptone | 17.5 |
| Starch | 1.5 |
| Meat extract | 4 |
| Agar | 15 |

Preparation:

22.5 g of the formulated product are dissolved in 1 L of distilled water and boiled. pH is adjusted to 7.3±0.2 at 25° C. and autoclaved for 15 minutes at 121° C.

During testing, the medium was stored in thermostatic bath between 45-50° C. because the seeding technique requires imbibing and integrating bacteria in the medium. Once solidified, the plates were incubated in inverted position for a set time of 24-48 hours prior to each count for the purposes of assessing the effective concentrations in each case and comparing with other treatments.

Example 4

Bactericidal effectiveness of IBU Na and IBU-H solutions in *P. aeruginosa* The test results are shown with IBU-Na and IBU-H solutions at different molar increasing concentrations on a population of *P. aeruginosa* at an incubation time of 4 h at 37° C. and subsequent seeding.

To perform the test of bactericidal effectiveness of the solution of IBU-H a final concentration of ethanol EtOH <5% was ensured to prevent the bactericidal action of the solvent itself.

| IBU | *P. aeruginosa* (UFC/mL ± 10) | |
|---|---|---|
| [mM] | IBU-Na | IBU-H. |
| 0 (Control) | 1,700,000 | 1,700,000 |
| 1 | 1,700,000 | 1,700,000 |
| 5 | 1,700,000 | 1,700,000 |
| 10 | 760,000 | 480,000 |
| 20 | 300,000 | 200,000 |
| 50 | 50 | 1000 |
| 100 | 10 | 10 |

Figure 3:
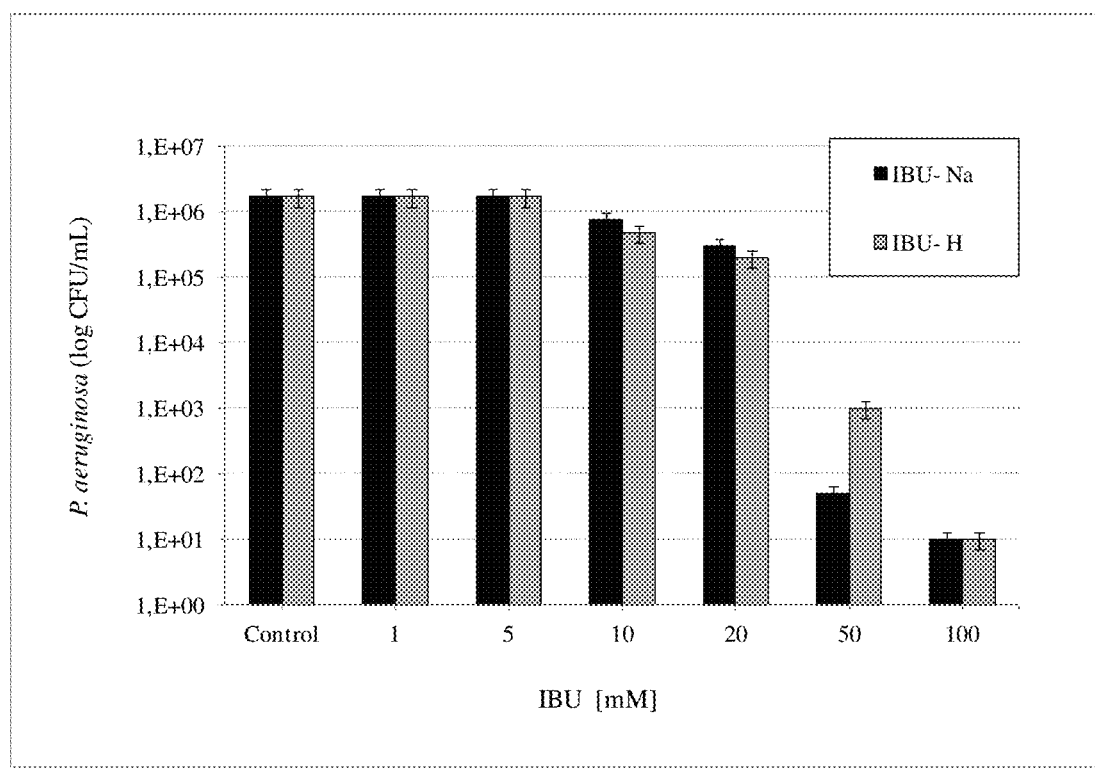
FIG. 3: Results from Example 4: Bactericidal effectiveness of solutions of SODIUM IBUPROFEN (SODIUM IBUPROFENATE or IBUPROFEN SODIUM SALT) IBU-Na and IBUPROFEN (PROTONATED IBUPROFEN) IBU-H in *P. aeruginosa*

See FIG. 3, where the results of this test shown that IBU-Na has a higher bactericidal capacity than IBU-H.

Example 5

Bactericidal Effectiveness of IBU-Na Solutions

In this example, the results shown correspond to a test with IBU-Na solutions at different increasing molar concentrations on three populations of the same strain (*P. aeruginosa*) for an incubation time of 4 h at 37° C. and subsequent plating.

| IBU-Na | *P. aeruginosa* (UFC/mL ± 10) | | |
|---|---|---|---|
| [mM] | Population A | Population B | Population C |
| 0 (Control) | 200,000 | 20,000 | 2,000 |
| 1 | 200,000 | 20,000 | 2,000 |
| 5 | 150,000 | 17,000 | 1,800 |
| 10 | 100,000 | 3,500 | 800 |
| 20 | 20,000 | 400 | 50 |
| 30 | 500 | 40 | 10 |
| 40 | 100 | 10 | 10 |
| 50 | 10 | 10 | 10 |
| 100 | 10 | 10 | 10 |

Figure 4:
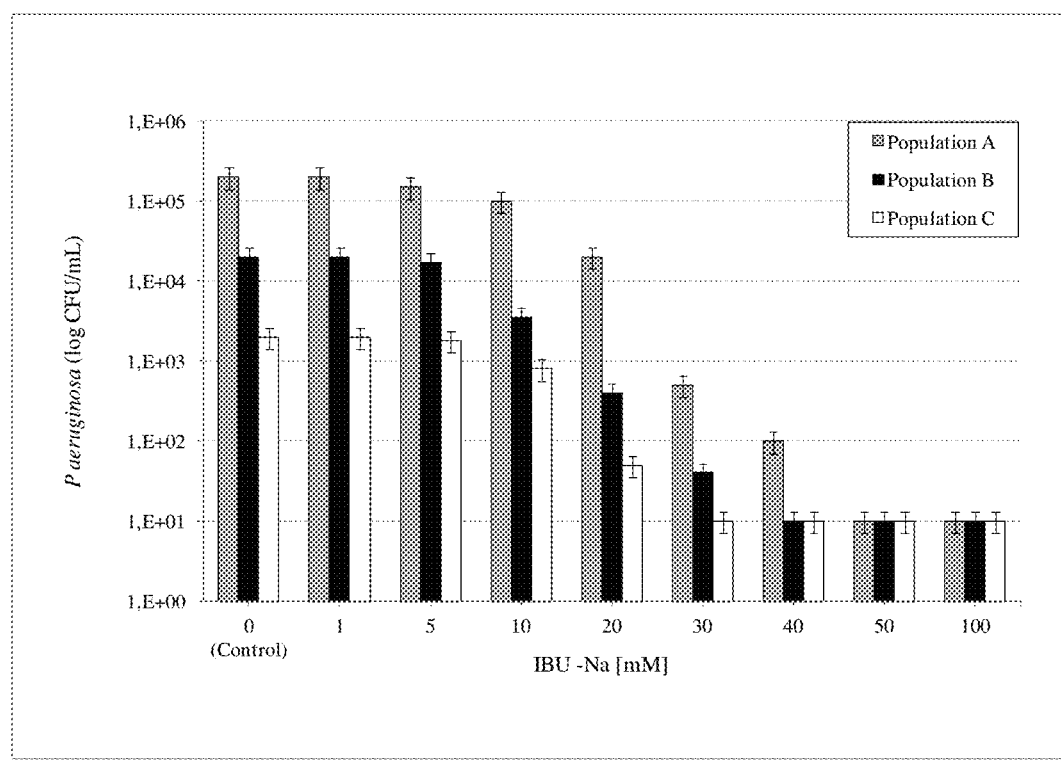
FIG. 4: Results from Example 5: Bactericidal effectiveness of IBU-Na solutions.

As shown in FIG. 4, this study concludes that the effective dose of IBU-Na depends on the bacterial load.

Example 6

Antimicrobial Effect of IBU-Na on *P. Aeruginosa* as a Function of Time.

The effect of IBU-Na on the same strain of *P. aeruginosa* at a fixed concentration of bacteria varying the concentration and contact time was characterized. The test was performed at 37° C. and subsequently the samples were plated.

| IBU-Na | *P. aeruginosa* count (UFC/mL ± 10) As a function of treatment time | | |
|---|---|---|---|
| [mM] | 1 hour | 4 hours | Overnight (O.N.) |
| 0 (Control) | 2,000,000 | 2,000,000 | 2,000,000 |
| 1 | 2,000,000 | 2,000,000 | 2,000,000 |
| 2.5 | 2,000,000 | 1,800,000 | 2,000,000 |
| 5 | 1,700,000 | 1,300,000 | 1,000,000 |
| 10 | 1,000,000 | 1,000,000 | 900,000 |
| 25 | 500,000 | 250,000 | 100,000 |
| 50 | 100,000 | 30 | 10 |
| 100 | 2,000 | 10 | 10 |

Figure 5:
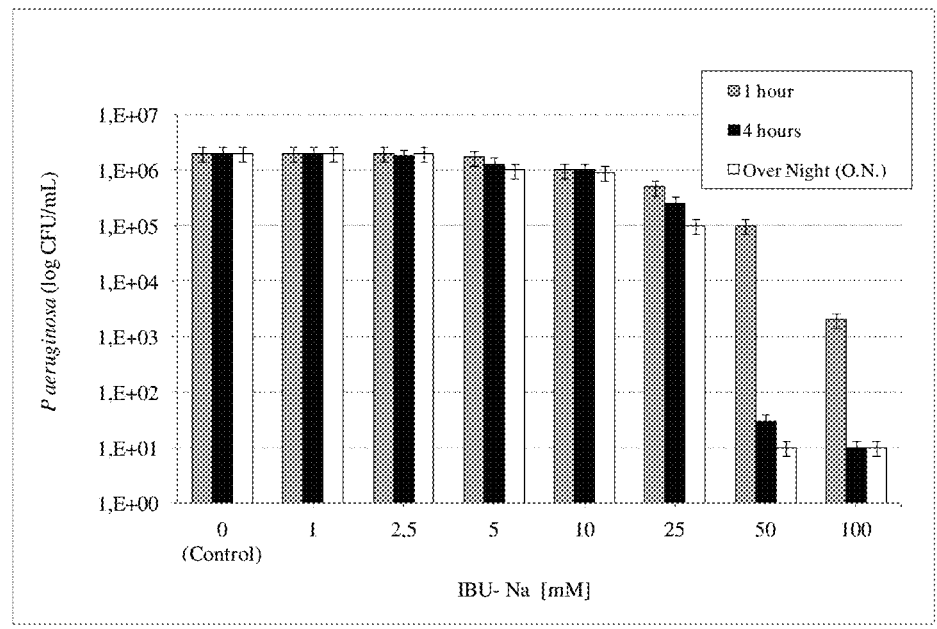
FIG. 5: Results from Example 6: Antimicrobial effect of IBU-Na on *P. aeruginosa* as a function of time.

As it can be seen in FIG. 5, these results show that certain IBU Na contact or treatment time is required to obtain antimicrobial effects; it was standardized for most trials in 4 hours.

Example 7

Antimicrobial Effect of IBU-Na on *P. aeruginosa* at Different pH Values.

Study on the effect of pH of the incubation medium test on bactericidal potential of a 50 mM solution of NaIBU incubated for 4 h at 37° with an inoculum of *P. aeruginosa*

| IBU-Na | *P. aeruginosa* (UFC/mL ± 10) | | |
|---|---|---|---|
| [mM] | pH 6.8 | pH 7.3 | pH 7.8 |
| 0 (Control) | 200,000 | 200,000 | 200,000 |
| 50 | 10 | 10 | 600 |

Figure 6:
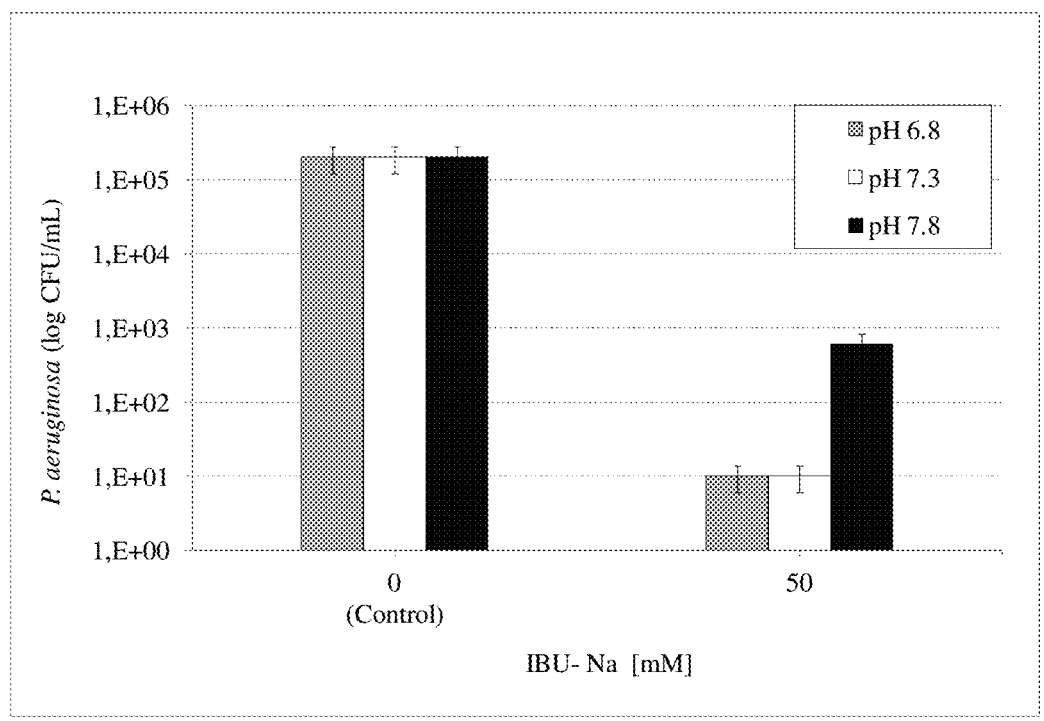
FIG. 6: Results from Example 7: Antimicrobial effect of IBU-Na on *P. aeruginosa* at different pH values.

As it can be seen in FIG. 6, the result shows that IBU-Na acts as an antimicrobial agent in the range of physiological pH values.

Example 8

Antimicrobial Effect of IBU-Na on Different Bacterial Strains

Antimicrobial effect of IBU-Na at two test concentrations [50 and 100 mM] on the viability of Gram positive and negative bacterial strains during 4-hour contact at 37° C.

| | Colony count (UFC/mL ± 10) | | |
|---|---|---|---|
| Microorganism | Controls | IBU-Na 50 mM | IBU-Na 100 mM |
| A Pseudomonas aeruginosa | 2,000,000 | 100 | 10 |
| B Burkhordelia cepacia | 1,300,000 | 680 | 10 |
| C Pseudomonas fluorescens | 100,000 | 150 | 10 |
| D Enterobacter aerogenes | 1,000,000 | 450 | 10 |
| E Klebsiella pneumoniae | 1,000,000 | 600 | 10 |
| F Escherichia coli | 1,000,000 | 500 | 10 |
| G Bacillus subtilis (Gram +) | 500,000 | 250 | 10 |
| H Staphylococcus aureus (Gram +) | 1,000,000 | 550 | 10 |
| I Enterococcus faecalis (Gram +) | 100,000 | 180 | 10 |

Figure 7:
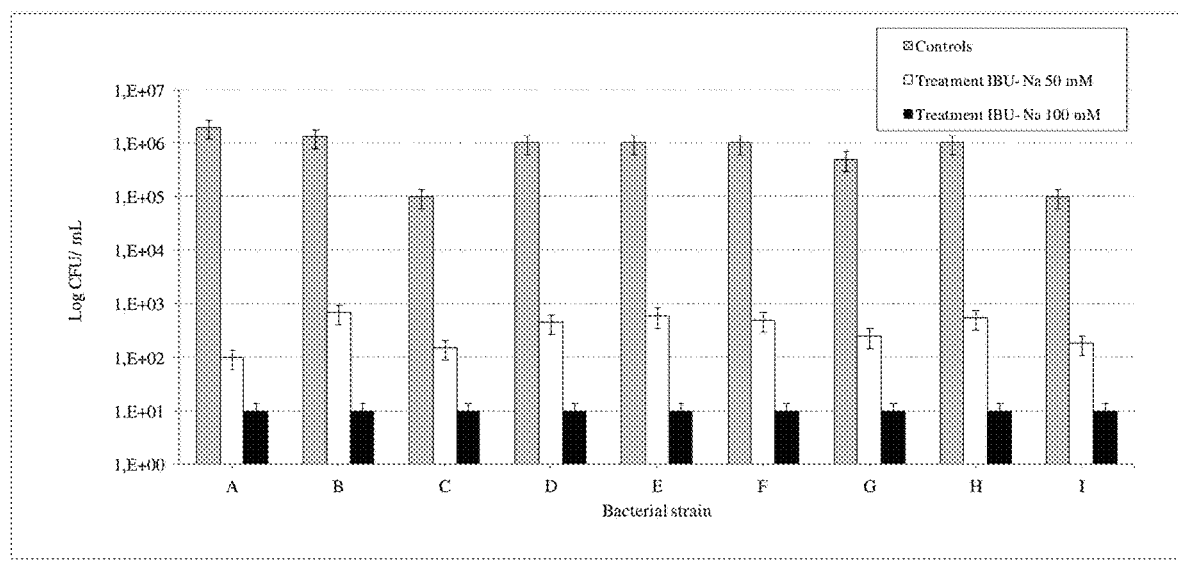
FIG. 7: Results from Example 8: Antimicrobial effect of IBU-Na on different bacterial strains

As it can be seen in FIG. 7, the result shows that IBU-Na acts an antimicrobial agent on different bacterial strains (Gram positive and negative ones).

Example 9

Antimicrobial Effect of IBU-Na at Various Concentrations on Three Main Bacterial Strains Associated with Cystic Fibrosis (CF).

Effect of IBU-Na at various concentrations on the viability of Staphylococcus aureus, Burkhordelia cepacia and Pseudomonas aeruginosa, for 4 hours at 37° C.

| IBU-Na [mM] | Colony count (UFC/mL ± 10) | | |
|---|---|---|---|
| | Staphylococcus | Burkhordelia | Pseudomonas |
| 0 (Control) | 1,000,000 | 1,300,000. | 1,700,000. |
| 5 | 1,000,000 | 1,300,000 | 1,700,000 |
| 10 | 1,000,000 | 1,300,000 | 760,000 |
| 25 | 30,000 | 40,000 | 200,000 |
| 50 | 600 | 700 | 100 |
| 100 | 10 | 10 | 10 |

Figure 8:
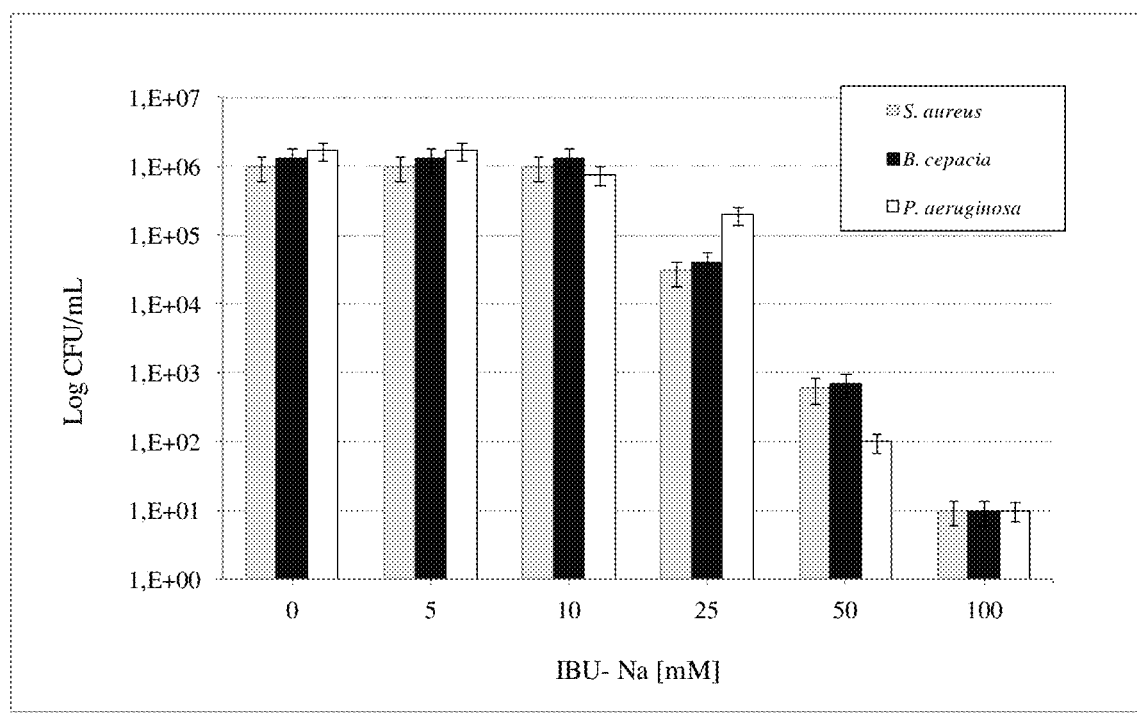
FIG. 8: Results from Example 9: Antimicrobial effect of IBU-Na at various concentrations on three main bacterial strains that are associated with Cystic Fibrosis (CF).

The result shows that IBU-Na has effect on the three most common bacterial strains which are found in cystic fibrosis (FIG. 8)

Example 10

Antimicrobial Effect of Naproxen on a Population of Burkhordelia cepacia.

In this study, the effect of naproxen on a population of B. cepacia strain was analyzed at different concentrations, testing for 4 h incubation at 37° C.

| Naproxen [mM] | B. cepacia (UFC/mL ± 10) |
|---|---|
| 0 (Control) | 130,000 |
| 10 | 125,000 |
| 25 | 38,000 |
| 50 | 31,000 |
| 100 | 1,300 |

Figure 9:
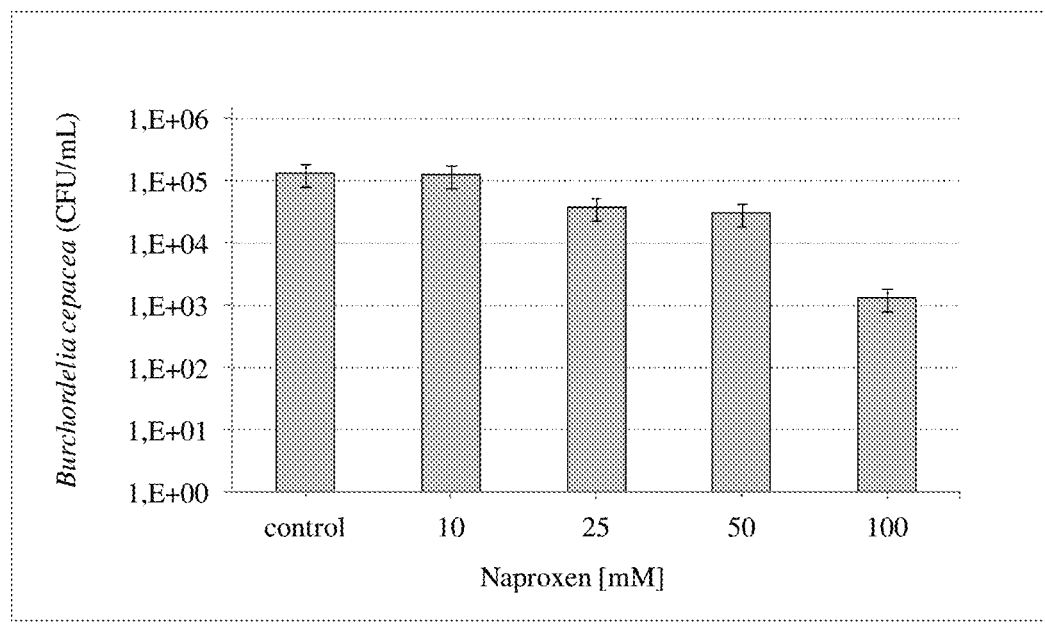
FIG. 9: Results from Example 10: Antimicrobial effect of naproxen on a population of *Burkhordelia cepacia*.

As shown in FIG. 9. The result shows that naproxen shows less antimicrobial activity compared with IBU-Na.

Example 11

Effect of Ionic Strength (NaCl) on a Culture of P. aeruginosa.

In this study the effect of the ionic strength (NaCl) on a culture of P. aeruginosa is analyzed at different concentrations in treatments lasting 4 hours at 37° C.

| NaCl [M] | P. aeruginosa (UFC/mL ± 10) |
|---|---|
| 0 (Control) | 2,000,000 |
| 0.01 | 2,000,000 |
| 0.025 | 2,000,000 |
| 0.05 | 2,000,000 |
| 0.1 | 2,000,000 |
| 0.25 | 1,800,000 |
| 0.5 | 1,600,000 |
| 1 | 1,000,000 |

Figure 10:
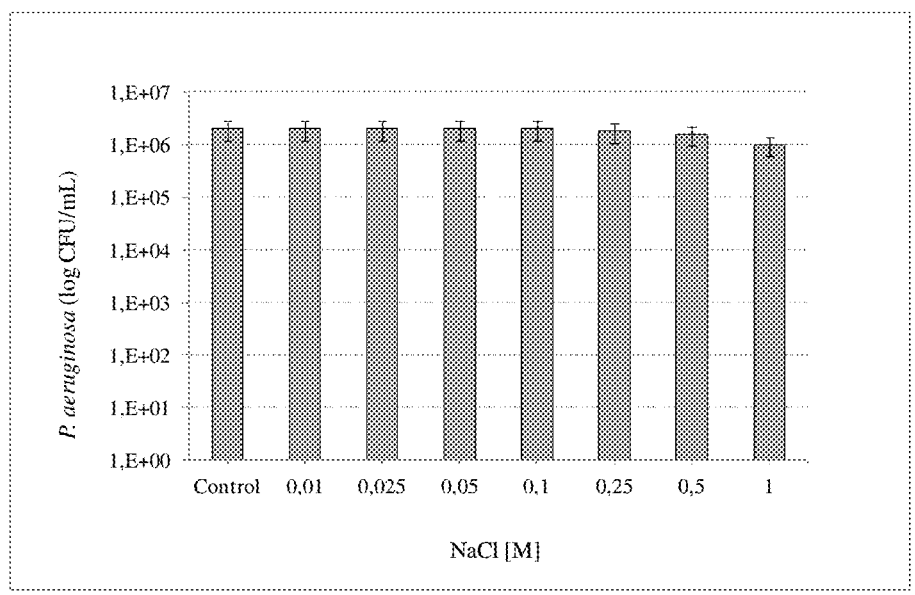
FIG. 10: Results from Example 11: Effect of ionic strength (NaCl) on a culture of *P. aeruginosa*.

No decrease was observed in the bacterial population as a result of the effects of ionic strength. (FIG. 10)

Example 12

Effect of the Composition of the Present Invention Comprising IBU-Na with Ionic Strength (1M NaCl) on a Culture of P. aeruginosa.

Study to evaluate the bactericidal effect in the presence IBU-Na ionic strength (1 M NaCl) on a P. aeruginosa culture for 4 hours at 37° C.

| IBU-Na [mM] | P. aeruginosa (UFC/mL ± 10) | |
|---|---|---|
| | ionic strength NaCl (1M) | Without ionic strength |
| 0 (Control) | 1,700,000 | 1,700,000 |
| 5 | 1,000 | 1,700,000 |
| 10 | 10 | 760,000 |
| 25 | 10 | 200,000 |
| 50 | 10 | 100 |

Figure 11:
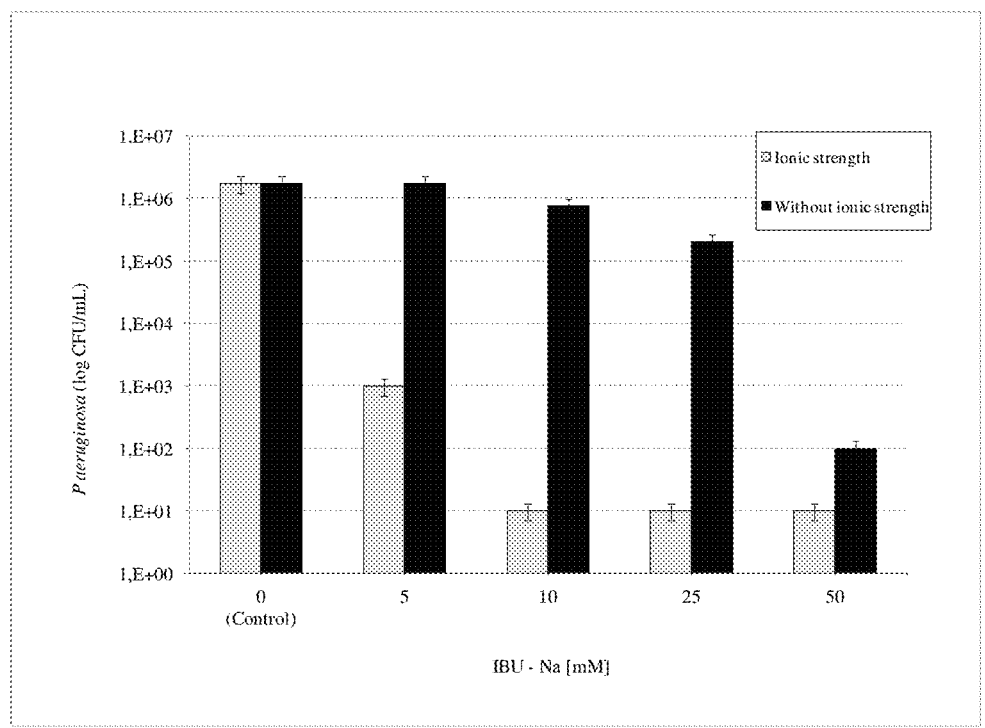
FIG. 11: Results from Example 12: Effect of the composition of the present invention comprising IBU-Na with ionic strength (1M NaCl) on a culture of *P. aeruginosa*.

The result clearly shows that ionic strength enhances the action of the IBU-Na, reducing the needed dose to obtain antimicrobial effects on the population of bacteria tested. FIG. 11 shows clearly that with a concentration of 25 mM of IBU-Na the number of CFU/mL decreases to 1000, while the composition of the present invention with ionic strength of NaCl to 1 M the same result is obtained at a concentration five times lower, i.e., about 5 mM Na-IBU.

Example 13

Bactericidal Effect of the Composition of the Present Invention, Comprising a Hypertonic Solution of Ibuprofen as a Function of Time.

Following, the study to evaluate the bactericidal effect IBU-Na in the presence of ionic strength (1M NaCl) at different times of incubation on a culture of P. aeruginosa is shown. The treatments lasted 1 hour, 2 hours and 4 hours at 37° C. pH 6.5.

| IBU-Na [mM] + ClNa (1M) | P. aeruginosa (UFC/mL ± 10) | | |
|---|---|---|---|
| | 1 hour | 2 hours | 4 hours |
| 0 (Control) | 800,000 | 800,000 | 800,000 |
| 5 | 16,000 | 13,000 | 8,500 |
| 10 | 30 | 30 | 10 |
| 20 | 10 | 10 | 10 |

Figure 12:
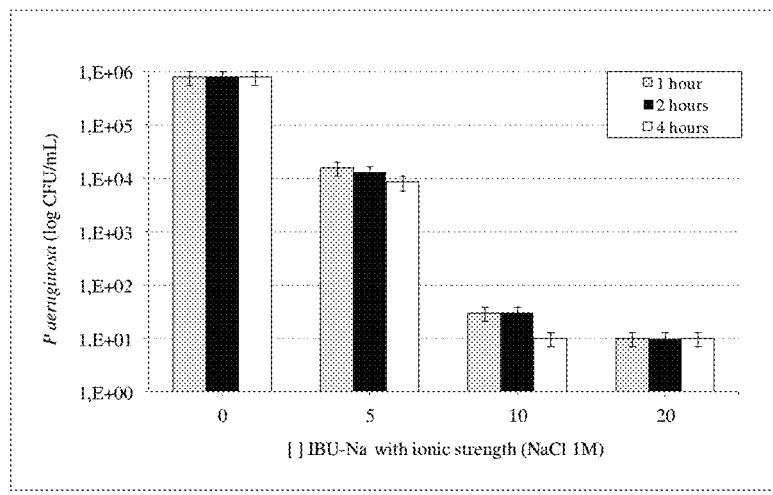
FIG. 12: Results from Example 13: Bactericidal effect of the composition of the present invention, comprising a hypertonic solution of ibuprofen as a function of time.

As seen in FIG. 12, this result shows that ion strength can shorten action times previously set.

Example 14

Effect of the Composition of the Present Invention Comprising IBU-Na with Ionic Strength on a Culture of *P. aeruginosa* Varying Treatment Time (in Minutes).

This study shows the bactericidal effect of IBU-Na 20 mM in the presence of ionic strength (1M NaCl) on a culture of *P. aeruginosa*. Treatments at different incubation times (1, 3 and 10 minutes)

| | *P. aeruginosa* (UFC/mL ± 10) | | |
|---|---|---|---|
| Time (Minutes) | IBU 20 mM with ionic strength | IBU 20 mM without ionic strength | Preincubation 10' with ionic strength Posterior: IBU 20 mM |
| 0 (Control) | 1,000,000 | 1,000,000 | 1,000,000 |
| 1 | 10 | 1,000,000 | 1,000,000 |
| 3 | 10 | 1,000,000 | 1,000,000 |
| 10 | 10 | 1,000,000 | 1,000,000 |

Figure 13:
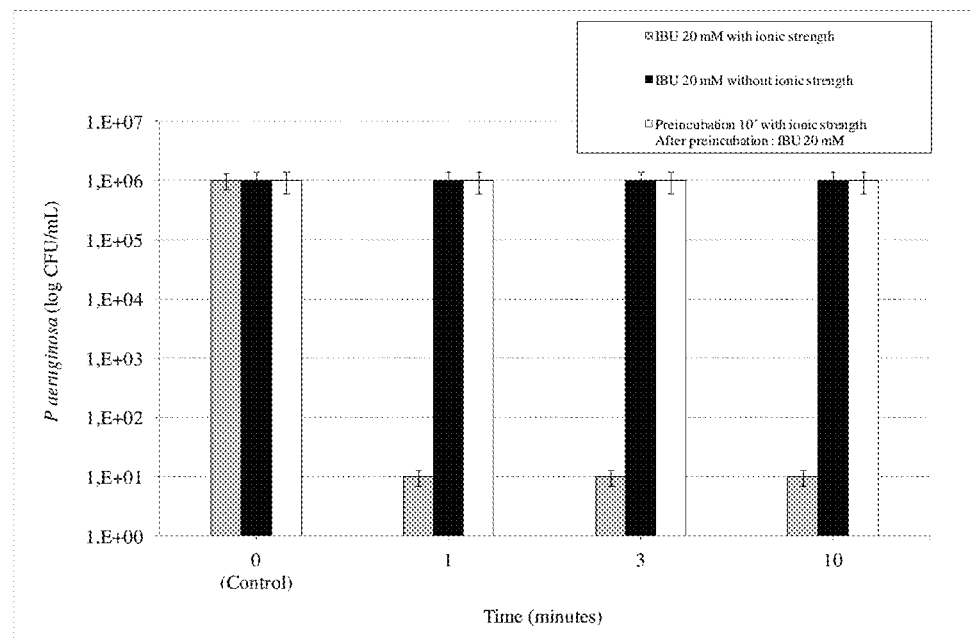
FIG. 13: Results from Example 14: Effect of the composition of the present invention comprising IBU-Na with ionic strength on a culture of *P. aeruginosa* varying treatment time (minutes).

As seen in FIG. 13, the result shows that only the combined treatment of ibuprofen in the presence of ionic strength (IBU-Na 20 mM+NaCl 1 M) allows a synergistic result on the antimicrobial effect as a function of time.
Analyzing other alternatives, as shown in the third and fourth column of the table in this same example with ibuprofen alone without ionic strength and a dissociated treatment preincubating an inoculum of *P. aeruginosa* 1×10 8 CFU/mL for 10 minutes ClNa 1 M and subsequent washing by dilution 1/10 in buffer containing 20 mM IBU. As a result it is stated that just ionic strength alone does not affect the inoculum; the ionic strength pretreatment and subsequent treatment with ibuprofen did not cause changes in the inoculum compared with the controls, as shown in the fourth column of the table in this example. As evidenced in this example, the present invention has an unexpected and surprising technical effect, by achieving an almost instant synergistic effect (in relation to other therapeutic options) that promotes the interaction of ibuprofen on microorganisms, and thus in just one minute achieving a dramatic decrease of the population of microorganisms typical of cystic fibrosis.

Example 15

Effect of the Composition of the Present Invention Comprising Ibuprofen (IBU-Na) with Ionic Strength (1M NaCl) on a Culture of Three Bacterial Strains.

Test to evaluate the effect of IBU-Na with ionic strength (1M NaCl) on 3 bacterial strains: *P aeruginosa*, *S aureus* and *B cepacia* in 4-hour treatments at 37° C.

| IBU-Na [mM] + ClNa (1M) | Colony count (UFC/mL ± 10) | | |
|---|---|---|---|
| | *P. aeruginosa* | *S. aureus* | *B. cepacia* |
| 0 | 3,000,000 | 1,000,000 | 1,700,000 |
| 12.5 | 250 | 100 | 100 |
| 25 | 10 | 10 | 10 |
| 50 | 10 | 10 | 10 |

Figure 14:
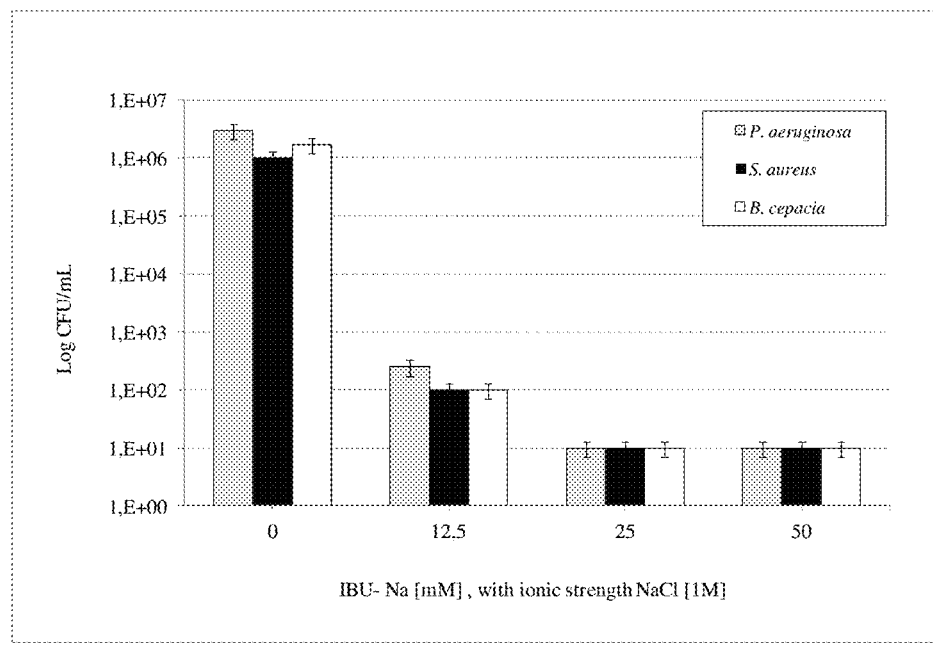
FIG. 14: Results from Example 15: Effect of the composition of the present invention comprising ibuprofen (IBU-Na) with ionic strength (1M NaCl) on a culture of three bacterial strains.

As seen in FIG. 14, the presence of a hypertonic solution favors the antibacterial action of IBU-Na on the three strains of interest associated with CF.

Next, application examples are given to show how the bactericidal effect of ibuprofen is affected when administered orally or intravenously. These examples show aspects that evidence the high inventive step of the present composition, since it provides a formulation, which avoids factors that have usually hidden the bactericidal effects of ibuprofen.

Example 16

Effect of the Presence of Human Albumin on the Bactericidal Activity of IBU-Na [20 mM] in Medium with Ionic Strength (1M NaCl).

Study to evaluate the effect of the presence of a serum protein, human albumin, known for its ability to interact strongly with the ibuprofen molecule on the bactericidal activity. In this case the initial pre-incubation was performed at room temperature for 1 hour, with different concentrations of Albumin IBU-Na [20 mM]; they were subsequently incubated with the bacteria in the presence of ionic strength (1 M NaCl) to start the final treatment lasting 4 hours at 37° C.

| Albumin (mg/mL) with IBU 20 mM y NaCl (1M) | *P. aeruginosa* (UFC/mL ± 10) |
|---|---|
| Control* | 1,000,000 |
| 10 | 1,000,000 |
| 5 | 1500 |
| 2.5 | 10 |

*Albumin 10 mg/mL without IBU-Na

Figure 15:
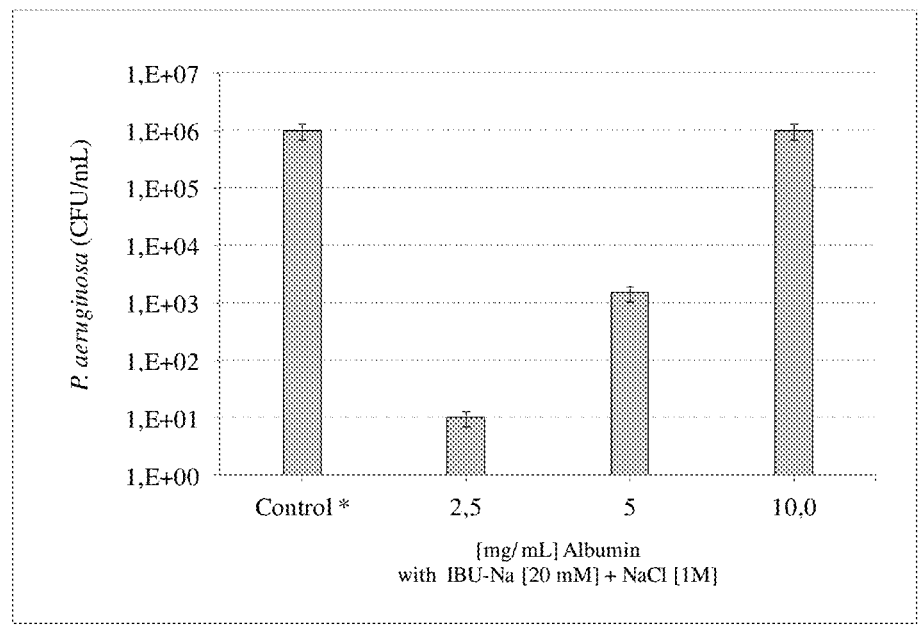
FIG. 15: Results from Example 16: Effect of the presence of human albumin on the bactericidal activity of IBU-Na [20 m] in medium ionic strength (1M NaCl).

As it can be seen in FIG. 15, the presence of albumin interferes with the antibacterial action of 20 mM IBU-Na. From albumin concentrations below 10 mg/mL the bactericidal effect of IBU-Na, starts recovering, which suggests some sort of interaction.

Example 17

Effect of LIPOVENOS™ (Medium Chain Triglycerides) in the Presence of Ionic Strength (1 M NaCl) on a Culture of *P. aeruginosa*.

An inoculum of *P. aeruginosa* was incubated in the presence of LIPOVENOS™+ionic strength (1 M NaCl) during a 4-hour treatment at 37° C.

| LIPOVENOS % treatment with NaCl (1M) | *P. aeruginosa* (UFC/mL ± 10) |
|---|---|
| Control (0%) | 2,000,000 |
| 2.5% | 2,000,000 |
| 5% | 2,000,000 |
| 10% | 2,000,000 |
| 20% | 2,000,000 |

Figure 16:
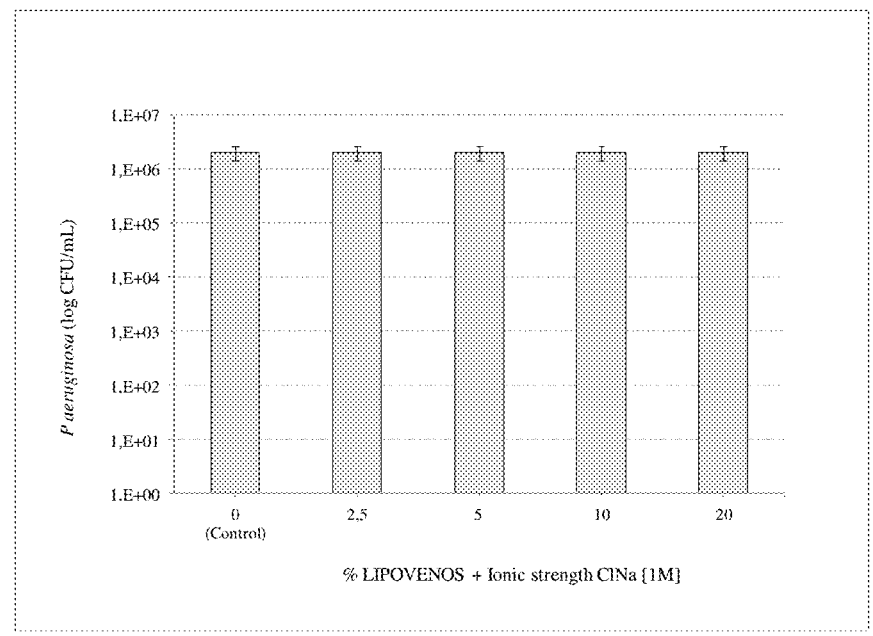
FIG. 16: Results from Example 17: Effect of LIPOVENOS in the presence of ionic strength (1 M NaCl) over a culture of *P. aeruginosa*.

As it can be seen in FIG. 16, LIPOVENOS™ has no effect on the inoculum at the concentrations tested.

Example 18

Effect of Na IBU-[20 mM] in the Presence of LIPOVENOS™ on the Viability of *P. aeruginosa*.

LIPOVENOS initial preincubation at different concentrations with IBU-Na 20 [mM] at room temperature for 1 hour. It was subsequently mixed with bacteria to begin a treatment of 4 hours at 37° C.

| LIPOVENOS(%) + Ibu 20 mM | P. aeruginosa (UFC/mL ± 10) |
|---|---|
| Control* | 1,000,000 |
| LIPO 10% + IBU 20 Mm | 1,000,000 |
| LIPO 5% + IBU 20 Mm | 1,000,000 |
| LIPO 2.5% + IBU 20 Mm | 1,000,000 |

*LIPOVENOS$^{MR}$ 10%, without IBU-Na

The presence of LIPOVENOS™ up to 2.5%, exhibits a marked interference on the antibacterial action of IBU-Na 20 mM.

Example 19

Antimicrobial Effect of Tobramycin as a Function of Concentration and Contact Time on P. aeruginosa.

This test evaluated the activity of an antibiotic known as tobramycin on a population of P. aeruginosa in treatments lasting 1 h, 4 h and O.N. at 37° C. and thus compared studies of previous examples of ibuprofen activity.

| Tobramycin [mM] | P. aeruginosa (UFC/mL ± 10) | | |
|---|---|---|---|
| | 1 hour | 4 hours | O.N. |
| Control | 2,000,000 | 2,000,000 | 2,000,000 |
| 1 | 1,000,000 | 30,000 | 30,000 |
| 2.5 | 60,000 | 20,000 | 10 |
| 5 | 30,000 | 1,000 | 10 |
| 10 | 1,000 | 10 | 10 |

Figure 17:
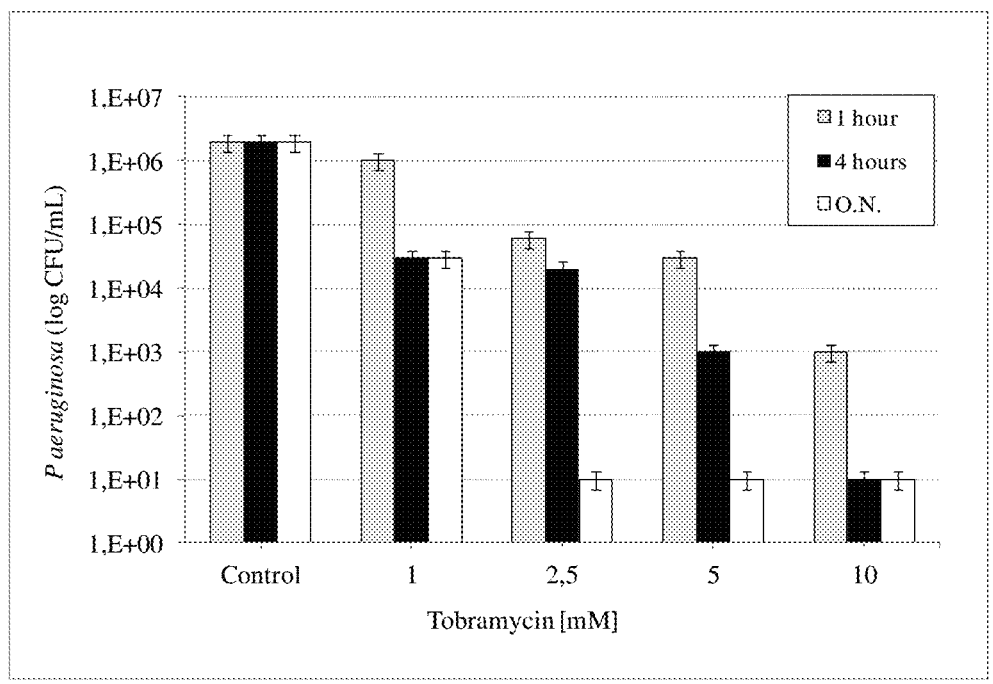
FIG. 17: Results from Example 19: Antimicrobial effect of tobramycin as a function of concentration and contact time on *P. aeruginosa*.

As it can be seen in FIG. 17, as bacteria and tobramycin antibiotic contact time increases, its bactericidal effect is enhanced.

Example 20

Antimicrobial Effect of Tobramycin in the Presence of Ionic Strength on P. aeruginosa.

This example shows an assay to assess a formulation of tobramycin antibiotic in the presence of 1 M NaCl solution on a population of P. aeruginosa for 4 h at 37° C.

| Tobramycin [mM] with ClNa (1M) | P. aeruginosa (UFC/mL ± 10) |
|---|---|
| 0 | 1,000,000 |
| 0.25 | 400,000 |
| 1 | 10 |
| 5 | 10 |
| 10 | 10 |

Figure 18:
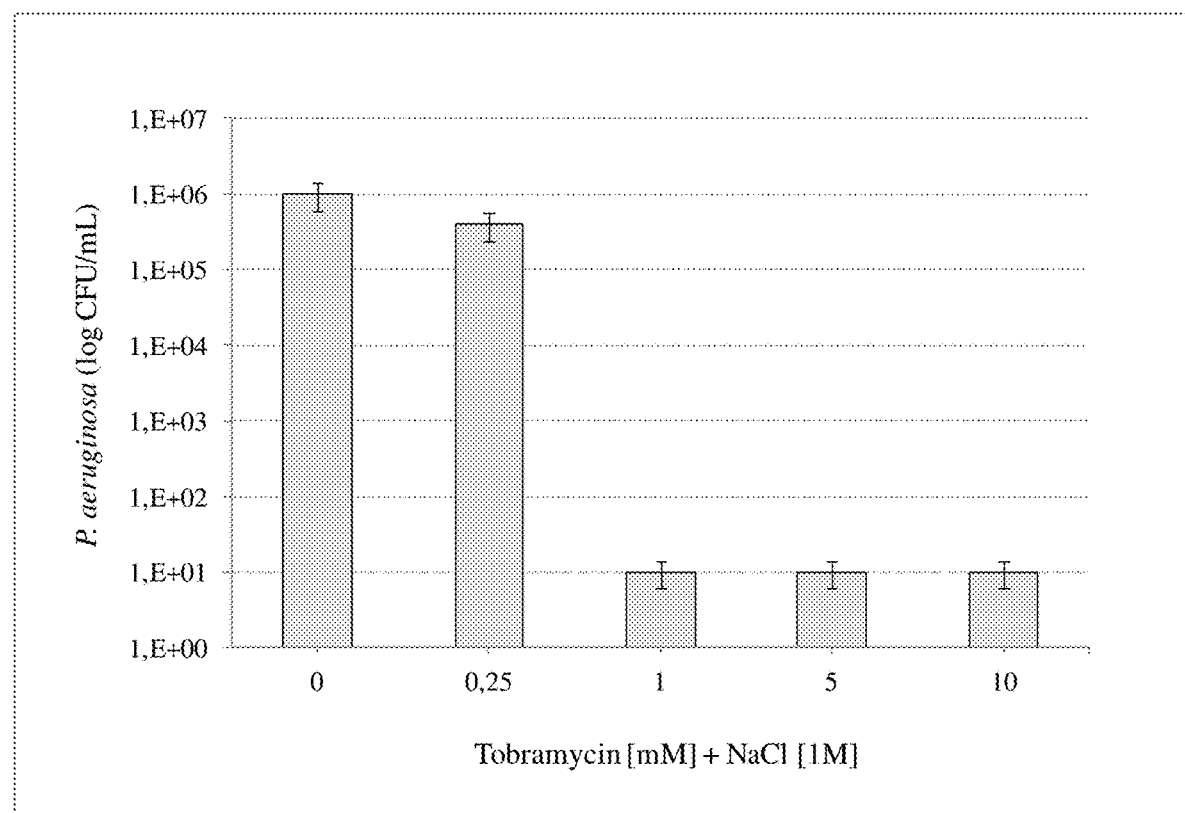
FIG. 18: Results from Example 20: Antimicrobial effect of tobramycin in the presence of ionic strength on *P. aeruginosa*.

As shown in FIG. 18, with the presence of ionic strength (1M NaCl) the bactericidal effect of antibiotic tobramycin is enhanced on a population of P. aeruginosa in a contact time of 4 h at 37° C.

Example 21

Antimicrobial Effect of IBU-Na and Tobramycin in the Presence of Ionic Strength on an Artificial Biofilm of P. aeruginosa.

Comparative study of the effect of IBU-Na and tobramycin in the presence of ionic strength (1 M NaCl) on an artificial biofilm of P. aeruginosa in the presence of 2% alginate solution. Treatments lasted 4 hours at 37° C.

| Treatments | P. aeruginosa (UFC/mL ± 10) |
|---|---|
| Biofilm Control | 2,000,000 |
| Biofilm + FI (1) | 2,000,000 |
| (1) + IBU-Na 10 mM | 25,000 |
| (1) + IBU-Na 25 mM | 200 |
| (1) + Tobramycin 5 mM* | 10 |
| (1) + Tobramycin 10 mM* | 10 |

*Formation of insoluble complex

Figure 19:
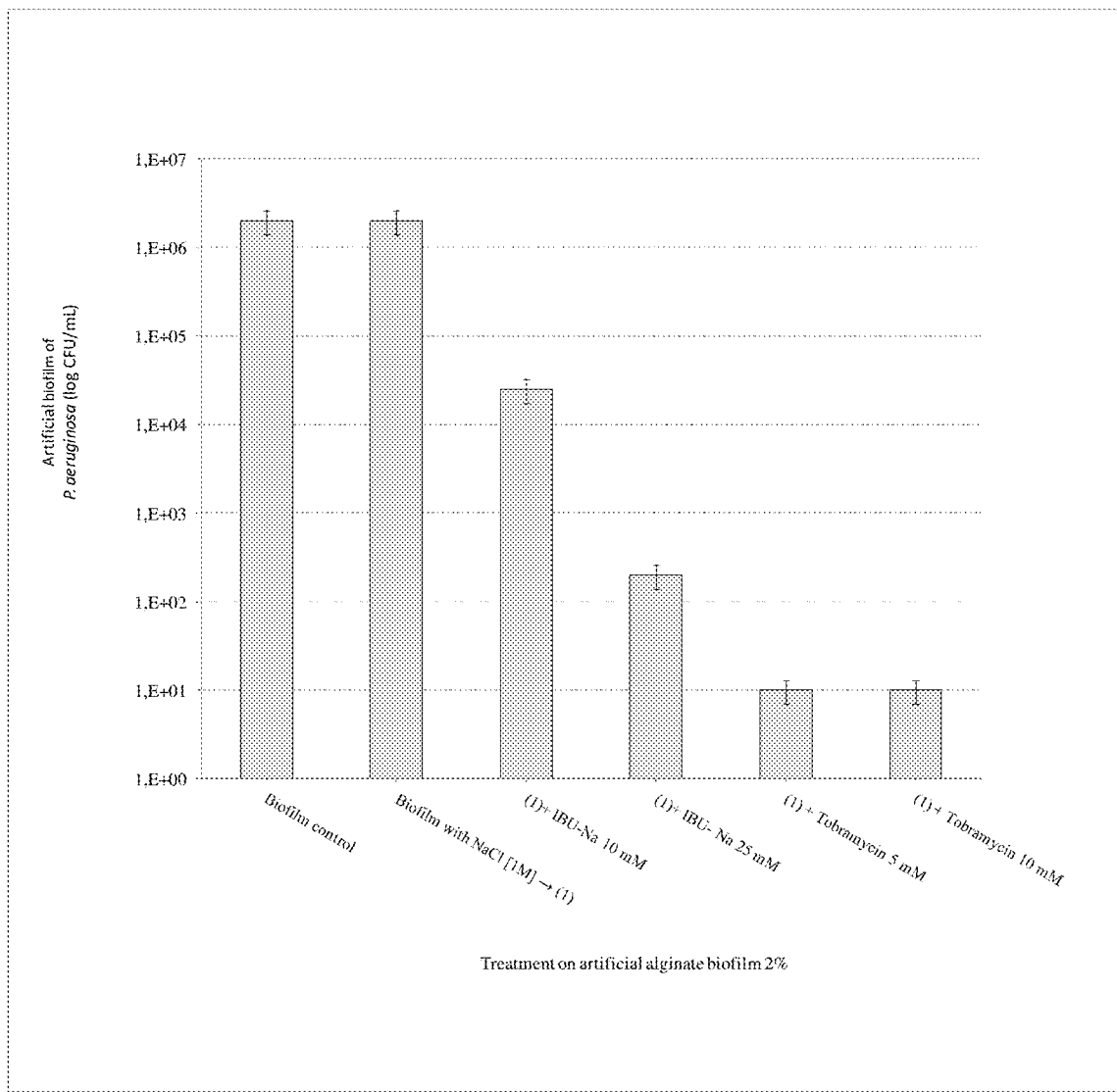
FIG. 19: Results from Example 21: Antimicrobial effect of IBU-Na and tobramycin in the presence of ionic strength on an artificial biofilm of *P. aeruginosa*.

As it can be seen in FIG. 19, the test shows that in the presence of ionic strength IBU-Na kept its antimicrobial properties despite the alginate barrier and did not form an insoluble complex. Whereas tobramycin formed an insoluble complex during the tests, but retained its effectiveness as an antibiotic.

It is worth highlighting that it is an insoluble compound which generates a progressive obstruction of the lungs in cystic fibrosis; Therefore, it is to be expected that when developing trials in humans the composition of the present invention is likely to constitute a recommended therapy for this disease.

Example 22

Evaluation of the Potential Cytotoxic Effect of Nebulised Ibuprofen in Two Concentrations on Lung Tissue in Rats.

This histopathological study analyzed the potential cytotoxic effect of ibuprofen potential on lungs at concentrations of 25 and 50 mM. Groups A and B correspond to replicated treatments with 8 animals at each concentration; these were nebulised 1 hour per day for 4 months. The remaining groups, C and D are similar to A and B, but after 4 months in each case they were allowed 15 days without any treatment and then sacrificed.

| Treatments | Doses IBU [mM] | Acute damage parameters | | | | | Damage parameters sub-acute | |
|---|---|---|---|---|---|---|---|---|
| | | Alveolar infiltration | Interstitial infiltration | Hyaline membranes | Proteinaceous material | septal thickening | Masson bodies | Granuloma and giant cells |
| A | 25 | 0 Alveolar Hemorrhage | 1 | 1 | 1 | 1 | NO | NO |
| | 50 | 0 Peribronchial mononuclear intense infiltrate | 0 Capillary congestion | 0 | 0 | 1 Scarce and focal | NO | NO |

-continued

| Treatments | Doses IBU [mM] | Acute damage parameters | | | | | Damage parameters sub-acute | |
|---|---|---|---|---|---|---|---|---|
| | | Alveolar infiltration | Interstitial infiltration | Hyaline membranes | Proteinaceous material | septal thickening | Masson bodies | Granuloma and giant cells |
| B | 25 | 0 | 1 | 0 | 0 | 1 | NO | NO |
| | 50 | 0 Peribronchial mononuclear intense infiltrate | 1 | 0 | 0 | 1 | NO | NO |
| C | 25 | 0 Peribonchiolar and perivascular mononuclear | 1 | 0 | 0 | 1 | NO | NO |
| | 50 | 0 Peribronchial mononuclear mild infiltrate | 1 | 0 | 0 | 1 | NO | NO |
| D | 25 | 0 Peribonchiolar and perivascular | 1 | 0 | 0 | 1 | NO | NO |
| | 50 | 0 Peribronchial mononuclear mild infiltrate | 1 | 0 | 0 | 1 | NO | NO |

From the results of anatomopathological studies shown in the table, it can be concluded that daily nebulisation of 60 minutes over 4 months, which is a relatively long period of time, a solution of ibuprofen 50 mM on Balb7c rat strains does not cause significant alterations on pulmonary tissue so as to render suspension necessary.

Example 23

Studies of Antiviral Activity of a Solution of Ibuprofen

There follows the description of in vitro studies where the activity of a solution of sodium ibuprofen is shown to cause the inactivation of viruses called "enveloped", which are those viruses having a lipid envelope.

Cell Culture Used in the Activity Assay

Kidney cells from African green monkey (Vero) (ATCC CCL-21), Madin Darby bovine kidney (MDBK) (ATCC CCL-22) cells and human cells from epithelial larynx tumor (Hep 2) (ATCC CCL-23) were propagated in minimal essential medium (MEM) supplemented with 10% fetal bovine serum irradiated containing 10000 IU of penicillin and 2 mM glutamine.

Viruses Used for Testing Inactivation

The BVDV bovine diarrhea virus was provided by INTA Castelar, and it was propagated in MDBK cell monolayers. The vesicular stomatitis virus (VSV) (ATCC VR-158) and Herpes Simplex 1 virus (HSV) were propagated in VERO cells. Rubella virus strain (MV) was obtained from the Rouvax commercial vaccine (Paster Merieux. France) was propagated in Hep-2 cells. The Herpes Simplex Virus (HSV) was provided by the Institute of Virology of the UNC, Universidad Nacional de Cordoba.

Virus Stock Preparation

Viruses were propagated using cells that are susceptible of infection, which were grown at 37° C., until complete destruction of the cell monolayer. Cell-associated viruses were extracted using three freeze-thaw cycles of the bottles that contained the cells. The material was centrifuged at 3000×g for 15 minutes and the supernatant was fractionated and stored at −70° C. until use.

Tests to Evaluate the Virucidal Activity of Ibuprofen and of the Composition of the Present Invention.

Infectivity assays of HSV, BVDV, VSV and MV virus: infectivity virus activity was determined by the titration method (by dilution 1/10) in 96-well plates (NUNC Life Technologies, Rockville, Md., USA), applying the criterion of measuring the cytopathic effect on cells (aggregation and cell death) and therefore positive or negative is determined. 1/10 serial dilutions of viruses were prepared in quadruplicate and incubated for 60 minutes at 37° C. stirring gently at different concentrations of ibuprofen ranging from 1 to 50 mM. After this period, the virus solution with ibuprofen is incubated in the presence of the cells and is also allowed to stand for 60 min. at 37° C. in order to allow the adsorption of the virus on the cells so they can exert their cytopathic effect. Then 150 uL of maintenance medium is added to each well without removing the inoculum.

Incubation was carried out at 37° C. in a stove containing 5% atmosphere of C02, 90% relative humidity for 3 days the case of HSV and VSV virus or up to 7 or 8 days for MV and BVDV virus, to allow sufficient time to detect the appearance of a potential cytopathic effect.

Determination of Infectious Dose 50

The so called Infectious Dose of cell culture 50% (TOD50 mL-1) was calculated by the Reed-Muench method of analysis (Reed L I, H. Munch, Am. J. Hygiene 1938 27, 493.) for wells infected by positive viruses.

Test Results on the Effect of Ibuprofen at 50 mM Concentration on the Infectivity of Viruses.

| | Virus | | | Reduction of viral level |
|---|---|---|---|---|
| | | Characteristics | | Ibuprofen |
| Virus | Family | Genome | Size (nM) | TCID50 mL−1 |
| HSV | Herpes | dsDNA | 120-200 | >6.9 |
| BVDV | Flavi | RssRNA | 50-70 | >6.5 |
| VSV | Rhabdo | SssRNA | 70-170 | >7.7 |
| MV | Paramyxo | SssRNA | 150-300 | >5.0 |

As it can be seen from the results obtained, incubation of ibuprofen in the presence of the enveloped viruses used, causes a marked inhibitory effect on the viral infectivity. Titers obtained expressed as Inhibitory Dosage 50, range from $10^5$ and $10^7$ log CFU.

What is claimed is:

1. A pharmaceutical composition comprising ibuprofen or a pharmaceutically acceptable salt thereof in a concentration from 5 to 50 mM solubilized in a hypertonic saline solution comprising between 0.3 M and 2 M sodium chloride.

2. The composition of claim 1, wherein the composition is in a form suitable for administration by inhalation or is in a form suitable for nebulization or is a mouthwash or is in a form suitable for topical administration.

3. The composition of claim 1, wherein said composition comprises a pharmaceutically acceptable salt of ibuprofen selected from the sodium salt of ibuprofen, the potassium salt of ibuprofen, the lithium salt of ibuprofen and a combination thereof.

4. The composition of claim 1, further comprising a pH in aqueous solution of between 6.0 and 8.5.

5. The composition of claim 1, further comprising an anesthetic agent.

6. The composition of claim 5, wherein said anesthetic agent is selected from the group consisting of xylocaine, lidocaine, mepivicaine and caricaine.

7. The composition of claim 1, wherein said composition comprises a state selected from the group consisting of liquid, powder and lyophilized state.

8. The composition of claim 1, wherein said composition is in a form suitable for nebulization.

9. The composition of claim 1, further comprising an antibiotic selected from the group consisting of colistimethate sodium, tobramycin, ciprofloxacin, lysine, levofloxacin, ciprofloxacin aztreonam, fosfomycin, amphotericin B, vancomycin, gentamicin, ceftazidime, ampicillin, amikacin and mixtures thereof.

10. The composition of claim 1, wherein a molar ratio of said ibuprofen or pharmaceutically acceptable salt thereof to sodium chloride of the hypertonic solution is between 1:0.6 and 1:400.

11. The pharmaceutical composition of claim 1, wherein the composition comprises the sodium salt of ibuprofen.

12. The pharmaceutical composition of claim 11, wherein the pH of the composition is between 6.0 and 8.5.

13. The pharmaceutical composition of claim 11, wherein the hypertonic saline solution comprises between 0.4 M and 1 M sodium chloride.

14. The pharmaceutical composition of claim 13, wherein the concentration of sodium ibuprofenate is 50 mM.

15. The pharmaceutical composition of claim 11, wherein the concentration of sodium ibuprofenate is 50 mM.

16. The pharmaceutical composition of claim 1, wherein the hypertonic saline solution comprises between 0.4 M and 1 M sodium chloride.

* * * * *